United States Patent
Cinar et al.

(10) Patent No.: US 8,690,820 B2
(45) Date of Patent: Apr. 8, 2014

(54) AUTOMATIC INSULIN PUMPS USING RECURSIVE MULTIVARIABLE MODELS AND ADAPTIVE CONTROL ALGORITHMS

(75) Inventors: Ali Cinar, Wilmette, IL (US); Meriyan Oruklu, Vernon Hills, IL (US)

(73) Assignee: Illinois Institute of Technology, Chicago, IL (US)

( * ) Notice: Subject to any disclaimer, the term of this patent is extended or adjusted under 35 U.S.C. 154(b) by 0 days.

(21) Appl. No.: 12/898,347

(22) Filed: Oct. 5, 2010

(65) Prior Publication Data

US 2011/0106011 A1    May 5, 2011

Related U.S. Application Data

(60) Provisional application No. 61/249,128, filed on Oct. 6, 2009.

(51) Int. Cl.
    *A61B 5/00*      (2006.01)
(52) U.S. Cl.
    USPC .............. 604/66; 604/151; 600/319; 600/365
(58) Field of Classification Search
    USPC ........ 604/65–66, 67; 600/315–316, 319–320, 600/346–347, 350, 365; 702/19
    See application file for complete search history.

(56) References Cited

U.S. PATENT DOCUMENTS

| | | | |
|---|---|---|---|
| 4,475,901 A * | 10/1984 | Kraegen et al. | 604/67 |
| 4,498,843 A | 2/1985 | Schneider et al. | |
| 6,572,542 B1 | 6/2003 | Houben et al. | |
| 7,402,153 B2 | 7/2008 | Steil et al. | |
| 2003/0050621 A1 | 3/2003 | Lebel et al. | |
| 2003/0114836 A1 | 6/2003 | Estes et al. | |
| 2003/0208113 A1 | 11/2003 | Mault et al. | |
| 2004/0034295 A1 * | 2/2004 | Salganicoff | 600/365 |
| 2005/0080322 A1 * | 4/2005 | Korman | 600/300 |
| 2005/0119540 A1 * | 6/2005 | Potts et al. | 600/315 |
| 2006/0079809 A1 * | 4/2006 | Goldberger et al. | 600/576 |
| 2007/0060870 A1 | 3/2007 | Tolle et al. | |
| 2007/0173761 A1 | 7/2007 | Kanderian, Jr. et al. | |
| 2007/0270672 A1 | 11/2007 | Hayter | |
| 2008/0014601 A1 * | 1/2008 | Goldberger et al. | 435/14 |

(Continued)

FOREIGN PATENT DOCUMENTS

| | | |
|---|---|---|
| EP | 1 177 802 A1 | 2/2002 |
| EP | 1 759 726 A2 | 3/2007 |

(Continued)

OTHER PUBLICATIONS

J. Schoborg et al., "Prediction of Future Glucose Concentrations Using Time-Series Models," Oct. 8, 2009, Biomedical Engineering Society Meeting, Pittsburgh, PA (Abstract).

(Continued)

*Primary Examiner* — Quynh-Nhu H Vu
(74) *Attorney, Agent, or Firm* — Pauley Petersen & Erickson

(57) ABSTRACT

A method and device for monitoring or treating patient glucose levels. The device includes a glucose sensor for measuring a glucose level of a patient, a physiological status monitoring system for measuring at least one physical or metabolic variable of the patient, and an automatic controller in communication with the glucose sensor and the physiological status monitoring system. The controller includes a prediction module for automatically predicting a future glucose level using data measured by the glucose sensor and the physiological sensor.

21 Claims, 15 Drawing Sheets

(56) References Cited

U.S. PATENT DOCUMENTS

| | | | |
|---|---|---|---|
| 2008/0188796 A1* | 8/2008 | Steil et al. | 604/66 |
| 2008/0300572 A1 | 12/2008 | Rankers et al. | |
| 2008/0306434 A1 | 12/2008 | Dobbles et al. | |
| 2009/0069787 A1 | 3/2009 | Estes et al. | |
| 2009/0227855 A1 | 9/2009 | Hill et al. | |
| 2009/0312621 A1* | 12/2009 | Verbitskiy et al. | 600/365 |
| 2011/0040487 A1* | 2/2011 | Hovorka | 702/19 |
| 2011/0046887 A1* | 2/2011 | Veldhuis et al. | 702/19 |

FOREIGN PATENT DOCUMENTS

| | | |
|---|---|---|
| WO | WO 96/37246 A1 | 11/1996 |
| WO | WO 00/74753 A1 | 12/2000 |
| WO | WO 2008/114254 A1 | 9/2008 |
| WO | WO 2008/135329 A1 | 11/2008 |
| WO | WO 2008/154312 A1 | 12/2008 |
| WO | WO 2009/023407 A1 | 2/2009 |

OTHER PUBLICATIONS

M. Eren-Oruklu, et al., "Adaptive Control Strategy for Regulation of Blood Glucose Levels in Patients with Type 1 Diabetes," J. Process Control, 19, pp. 1333-1346, Sep. 2009.

M. E. Eren-Oruklu, et al., "Estimation of Future Glucose Concentrations with Subject-Specific Recursive Linear Models," Diabetes Technol. Therapy, vol. 11, No. 4, pp. 234-241, Apr. 2009.

M. Eren-Oruklu, et al., "Blood Glucose Regulation with an Adaptive Model-Based Control Algorithm," Presentation at AIChE Annual Meeting, Nov. 16-21, 2008 (Abstract).

M. Eren-Oruklu, et al., "Blood Glucose Regulation for Patients with Type 1 Diabetes with an Augmented Self-Tuning Controller," Diabetes Technology Meeting, Bethesda, MD., Nov. 13-15, 2008 (Abstract).

M. Eren, et al., "Adaptive Control Strategy for Glucose Regulation Using Recursive Linear Models," IFAC Symp. Computer Applications in Biotechnology, Cancun, Mexico, Jun. 2007 (49 pages).

M. Eren-Oruklu, et al., "Self-Tuning Controller for Regulation of Glucose Levels in Patients with Type 1 Diabetes," Proc 2008 American control conference, Seattle, Washington, Jun. 2008 (6 pages).

M. Eren, et al., "Low-order Linear Dynamic Models for Prediction of Blook Glucose Concentration," Presentation at AIChE Annual Meeting, San Francisco, CA., 2006 (Abstract).

M. Eren, et al., "Automated Insulin Infusion and Blook Glucose Regulation by an Adaptive Control Strategy Using Patient's CGMS Data," Presentation at 2nd Chicago Diabetes Day, Chicago, IL., May 2007 (Abstract).

M. Eren, et al., "Prediction of Blook Glucose Concentration with Low-Order Linear and Recursive Models," BMES Meeting, Chicago, IL., Oct. 11-14, 2006 (Abstract).

M. Eren, et al., "Prediction of Blood Glucose Concentration with Low-Order Linear and Recursive Models," Presentation at 1st Chicago Diabetes Day, Chicago, IL., Jun. 2006 (Abstract).

* cited by examiner

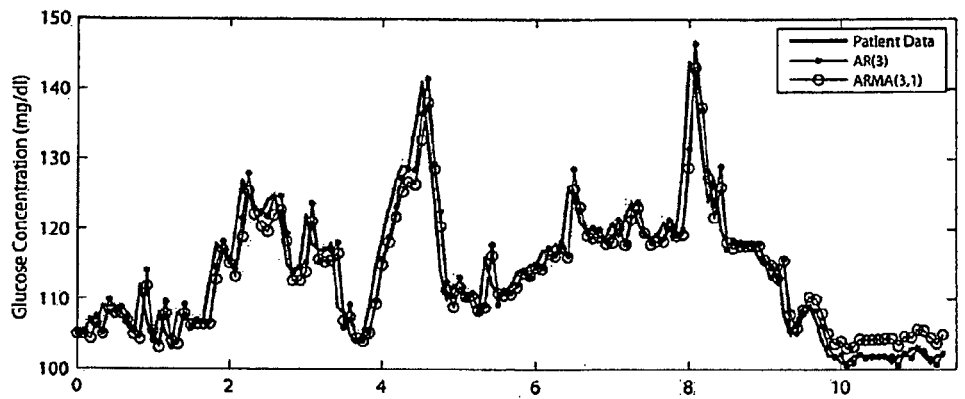
(a) Glucose Estimation for a Representative Healthy Subject
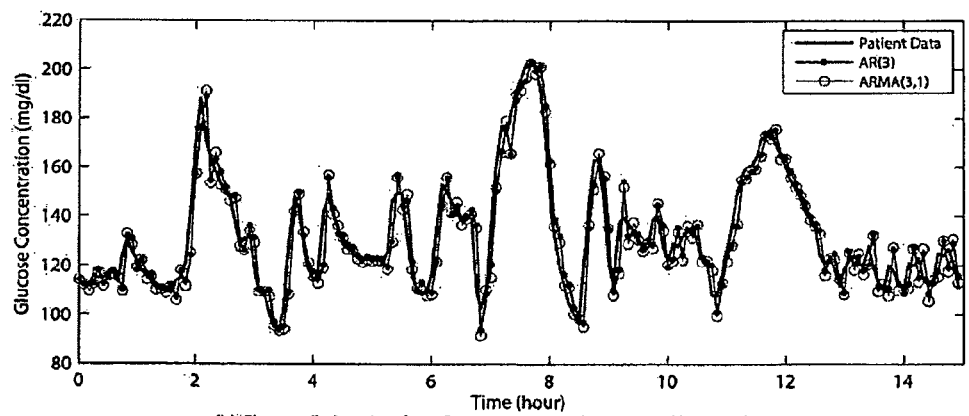
(b) Glucose Estimation for a Representative Glucose Intolerant Subject
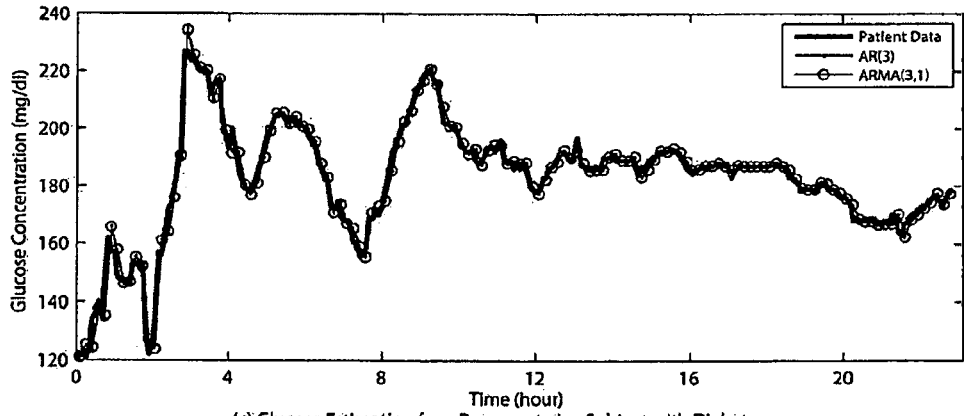
(c) Glucose Estimation for a Representative Subject with Diabetes
FIG. 4

TABLE 3
PREDICTION PERFORMANCES FOR SEVERAL PH VALUES USING TIME-INVARIANT MODELS: (A) SSGPE VALUES AND (B) RAD VALUES

| PH (step) | Group A | | | | | | Group B | | | | | |
|---|---|---|---|---|---|---|---|---|---|---|---|---|
| | Healthy | | Glucose-intolerant | | Diabetes | | Healthy | | Diabetes | | | |
| | AR(3) | ARMA(3,1) | AR(3) | ARMA(3,1) | AR(3) | ARMA(3,1) | AR(3) | ARMA(3,1) | AR(3) | ARMA(3,1) | | |
| (A) SSGPE (%) | | | | | | | | | | | | |
| 1 | 0.32 (0.12) | 0.24 (0.09) | 0.43 (0.16) | 0.31 (0.11) | 0.33 (0.15) | 0.25 (0.10) | 0.30 (0.08) | 0.21 (0.06) | 0.36 (0.16) | 0.27 (0.12) | | |
| 2 | 4.43 (0.72) | 4.40 (0.72) | 4.13 (1.06) | 4.07 (1.05) | 4.63 (1.24) | 4.59 (1.26) | 4.88 (1.69) | 4.83 (1.75) | 3.80 (2.05) | 3.73 (2.10) | | |
| 3 | 6.48 (1.02) | 6.45 (1.02) | 6.16 (1.47) | 6.06 (1.47) | 6.79 (1.73) | 6.73 (1.74) | 7.13 (2.11) | 7.03 (2.18) | 5.69 (2.59) | 5.58 (2.65) | | |
| 4 | 8.21 (1.24) | 8.17 (1.25) | 7.98 (1.76) | 7.84 (1.76) | 8.64 (2.10) | 8.57 (2.10) | 9.05 (2.29) | 8.84 (2.39) | 7.40 (2.82) | 7.21 (2.90) | | |
| 5 | 9.78 (1.41) | 9.73 (1.42) | 9.67 (1.98) | 9.51 (1.97) | 10.35 (2.45) | 10.26 (2.44) | 10.82 (2.38) | 10.46 (2.49) | 9.04 (2.92) | 8.78 (3.01) | | |
| 6 | 11.24 (1.55) | 11.19 (1.56) | 11.25 (2.15) | 11.08 (2.14) | 11.95 (2.80) | 11.90 (2.79) | 12.55 (2.43) | 11.97 (2.53) | 10.66 (2.95) | 10.32 (3.04) | | |
| (B) RAD (%) | | | | | | | | | | | | |
| 1 | 0.20 (0.08) | 0.15 (0.06) | 0.31 (0.13) | 0.23 (0.10) | 0.21 (0.11) | 0.16 (0.07) | 0.19 (0.07) | 0.15 (0.06) | 0.22 (0.10) | 0.17 (0.08) | | |
| 2 | 1.14 (0.22) | 1.08 (0.19) | 1.08 (0.40) | 0.97 (0.43) | 1.15 (0.52) | 1.07 (0.47) | 1.75 (0.46) | 1.75 (0.49) | 1.01 (0.33) | 0.95 (0.32) | | |
| 3 | 2.19 (0.39) | 2.11 (0.35) | 2.12 (0.68) | 2.07 (0.65) | 2.25 (1.05) | 2.15 (0.98) | 3.31 (0.71) | 3.30 (0.77) | 1.94 (0.60) | 1.85 (0.61) | | |
| 4 | 3.29 (0.56) | 3.21 (0.50) | 3.23 (0.97) | 3.15 (0.95) | 3.45 (1.62) | 3.35 (1.56) | 4.59 (0.83) | 4.55 (0.89) | 2.95 (0.90) | 2.83 (0.92) | | |
| 5 | 4.38 (0.71) | 4.31 (0.65) | 4.28 (1.32) | 4.20 (1.28) | 4.68 (2.20) | 4.62 (2.19) | 5.67 (0.97) | 5.64 (1.04) | 4.00 (1.22) | 3.87 (1.25) | | |
| 6 | 5.44 (0.83) | 5.40 (0.79) | 5.42 (1.68) | 5.29 (1.67) | 5.92 (2.78) | 5.90 (2.80) | 6.64 (1.06) | 6.58 (1.10) | 5.07 (1.56) | 4.93 (1.60) | | |

Data are population mean SSGPE and RAD values with standard deviations given in parentheses. Results are for time-invariant models. One step = 5 min.

FIG. 5

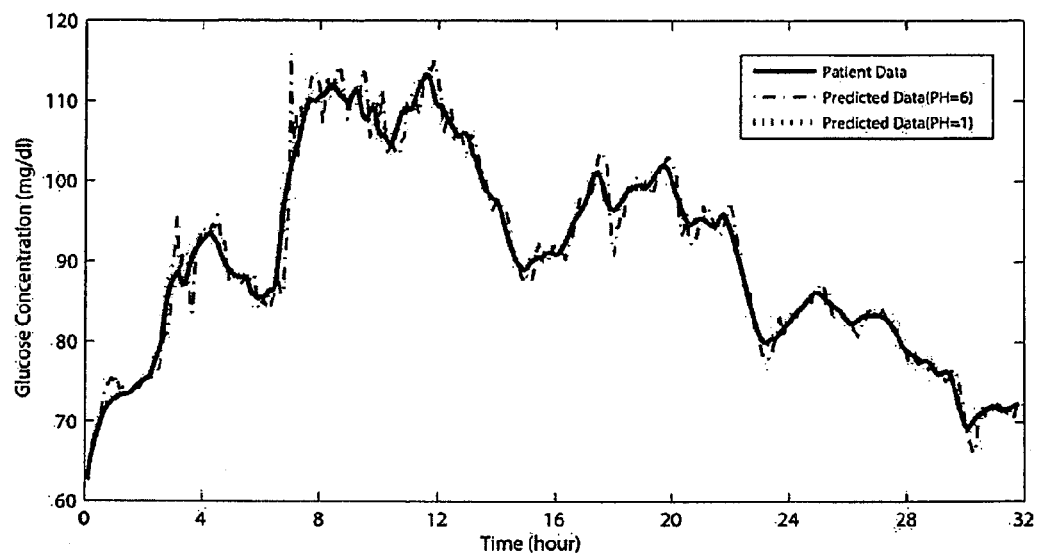
(a) Glucose Estimation for a Representative Healthy Subject
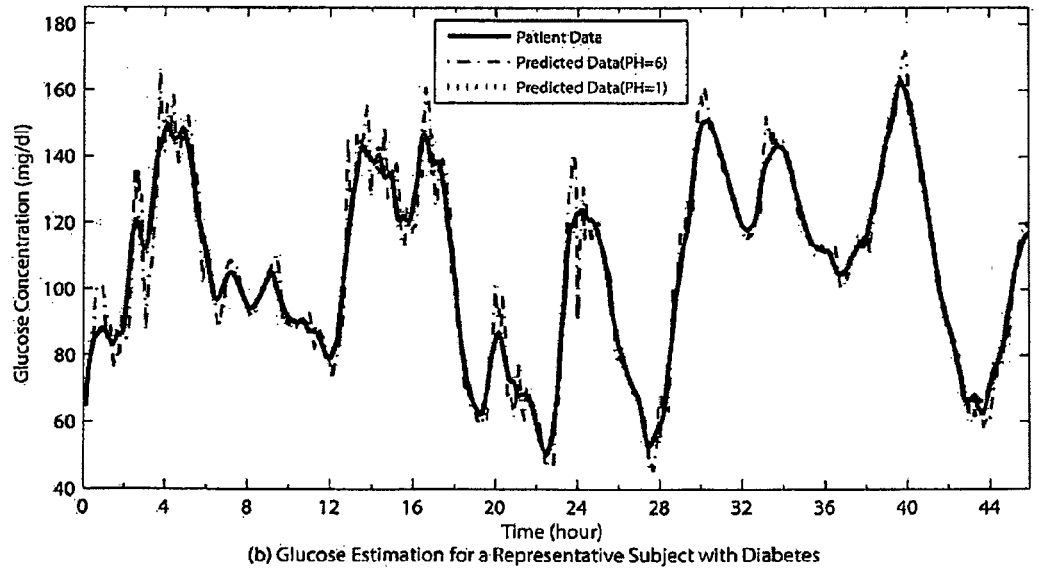
(b) Glucose Estimation for a Representative Subject with Diabetes
FIG. 6

TABLE 4
PREDICTION PERFORMANCES USING THE RECURSIVE ALGORITHM WITH AND WITHOUT THE CHANGE DETECTION STRATEGY:
(A) SSGPE VALUES (%) AND (B) RAD VALUES (%) (standard deviations given in parentheses)

| | Recursive algorithm | | | | | | | | | | | |
|---|---|---|---|---|---|---|---|---|---|---|---|---|
| | Group A | | | | | | Group B | | | | | |
| | Healthy | | Glucose-intolerant | | Diabetes | | Healthy | | Diabetes | | | |
| | Change direction | | Change direction | | Change direction | | Change direction | | Change direction | | | |
| PH (step) | With | Without | With | Without | With | Without | With | Without | With | Without | | |
| SSGPE | | | | | | | | | | | | |
| 1 | 0.32 (0.06) | 0.48 (0.15) | 0.50 (0.16) | 0.65 (0.18) | 0.42 (0.21) | 0.70 (0.24) | 0.35 (0.12) | 0.74 (0.38) | 0.45 (0.17) | 1.06 (0.45) | | |
| 2 | 0.91 (0.18) | 1.32 (0.40) | 1.50 (0.54) | 1.93 (0.54) | 1.22 (0.63) | 1.99 (0.65) | 1.02 (0.33) | 1.74 (1.03) | 1.32 (0.51) | 2.39 (0.86) | | |
| 3 | 1.80 (0.38) | 2.45 (0.75) | 3.00 (1.13) | 3.76 (1.51) | 2.44 (1.28) | 3.02 (1.08) | 1.95 (0.66) | 2.78 (1.72) | 2.57 (1.00) | 3.84 (1.42) | | |
| 4 | 2.57 (0.76) | 3.94 (1.25) | 4.12 (1.46) | 5.35 (1.76) | 4.16 (1.71) | 5.20 (1.94) | 2.95 (1.00) | 3.84 (1.44) | 4.28 (1.73) | 5.36 (2.04) | | |
| 5 | 2.84 (0.80) | 4.28 (1.42) | 4.75 (1.66) | 7.31 (1.97) | 4.35 (2.22) | 6.45 (2.74) | 3.16 (1.05) | 4.92 (2.18) | 4.90 (2.17) | 6.98 (2.76) | | |
| 6 | 3.02 (1.05) | 5.80 (1.96) | 5.42 (1.90) | 8.91 (2.51) | 5.30 (2.36) | 9.09 (3.65) | 3.60 (1.24) | 5.99 (2.23) | 5.56 (2.38) | 8.65 (3.52) | | |
| RAD | | | | | | | | | | | | |
| 1 | 0.25 (0.07) | 0.31 (0.10) | 0.39 (0.14) | 0.46 (0.13) | 0.29 (0.14) | 0.33 (0.16) | 0.25 (0.08) | 0.53 (0.23) | 0.32 (0.13) | 0.78 (0.33) | | |
| 2 | 0.69 (0.19) | 0.89 (0.28) | 1.15 (0.42) | 1.38 (0.41) | 0.85 (0.41) | 0.97 (0.46) | 0.73 (0.25) | 1.23 (0.58) | 0.94 (0.40) | 1.77 (0.66) | | |
| 3 | 1.32 (0.33) | 1.66 (0.54) | 2.24 (0.82) | 2.65 (0.80) | 1.69 (0.83) | 1.88 (0.90) | 1.39 (0.51) | 1.97 (0.97) | 1.81 (0.77) | 2.84 (1.07) | | |
| 4 | 2.11 (0.49) | 2.59 (0.85) | 3.04 (1.17) | 3.27 (1.25) | 2.64 (1.15) | 3.17 (1.33) | 2.22 (0.83) | 2.90 (1.22) | 2.90 (1.22) | 3.94 (1.50) | | |
| 5 | 2.17 (0.67) | 2.98 (0.66) | 3.21 (1.19) | 4.19 (1.25) | 2.94 (1.45) | 4.27 (2.16) | 2.39 (0.89) | 3.57 (1.60) | 3.57 (1.60) | 5.09 (1.97) | | |
| 6 | 2.55 (0.79) | 3.92 (0.90) | 3.67 (1.31) | 5.96 (1.76) | 3.53 (1.88) | 5.77 (2.86) | 2.70 (0.99) | 3.83 (1.63) | 3.83 (1.63) | 6.26 (2.44) | | |

Results are for a forgetting factor of 0.5 and $T_W$ = 5. One step = 5 min.

FIG. 7

TABLE 5
ERROR MATRIX OF CG-EGA FOR PREDICTED GLUCOSE VALUES WITH PH = 6 OF GROUP B:
(A) HEALTHY SUBGROUP AND (B) TYPE 2 DIABETES SUBGROUP

| Rate error grid zone | Point error grid zones ||||||||||||||
|---|---|---|---|---|---|---|---|---|---|---|---|---|---|
| | Hypoglycemia (BG ≤ 70 mg/dL) |||| Normoglycemia (70 < BG ≤ 180 mg/dL) ||| Hyperglycemia (BG > 180 mg/dL) |||||
| | A | D | E | A | B | C | A | B | C | D | E |
| (A) Healthy | | | | | | | | | | | |
| A | 92.31% | 0% | 0% | 85.17% | 0.46% | 0% | — | — | — | — | — |
| B | 0% | 0% | 0% | 9.52% | 0.32% | 0% | — | — | — | — | — |
| uC | 0% | 0% | 0% | 1.74% | 0.23% | 0% | — | — | — | — | — |
| lC | 7.69% | 0% | 0% | 2.29% | 0.27% | 0% | — | — | — | — | — |
| uD | 0% | 0% | 0% | 0% | 0% | 0% | — | — | — | — | — |
| lD | 0% | 0% | 0% | 0% | 0% | 0% | — | — | — | — | — |
| uE | 0% | 0% | 0% | 0% | 0% | 0% | — | — | — | — | — |
| lE | 0% | 0% | 0% | 0% | 0% | 0% | — | — | — | — | — |
| (B) Diabetes | | | | | | | | | | | |
| A | 81.76% | 1.18% | 0% | 72.43% | 1.18% | 0% | 70.23% | 1.00% | 0% | 0.08% | 0% |
| B | 11.18% | 0.59% | 0% | 17.05% | 0.84% | 0.04% | 18.23% | 0.33% | 0.17% | 0% | 0% |
| uC | 2.35% | 0% | 0% | 3.49% | 0.30% | 0% | 4.10% | 0.25% | 0% | 0% | 0% |
| lC | 2.94% | 0% | 0% | 3.58% | 0.25% | 0% | 4.01% | 0.17% | 0% | 0% | 0% |
| uD | 0% | 0% | 0% | 0.04% | 0% | 0% | 0.17% | 0% | 0% | 0% | 0% |
| lD | 0% | 0% | 0% | 0.04% | 0.17% | 0% | 0.08% | 0% | 0.17% | 0% | 0% |
| uE | 0% | 0% | 0% | 0.21% | 0% | 0% | 0.42% | 0% | 0% | 0% | 0% |
| lE | 0% | 0% | 0% | 0.30% | 0.08% | 0% | 0.59% | 0% | 0% | 0% | 0% |

The healthy subgroup had no measurements in the hyperglycemic range. The normal type, italic type, and bold type represent accurate readings, benign errors, and erroneous readings, respectively. BG, blood glucose.

FIG. 8

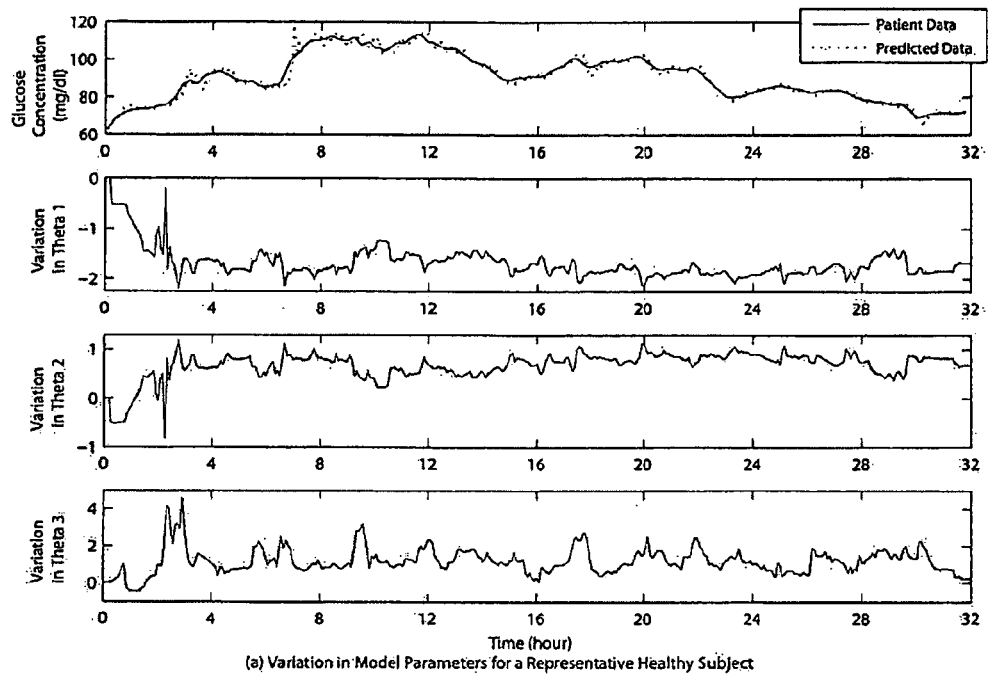
(a) Variation in Model Parameters for a Representative Healthy Subject
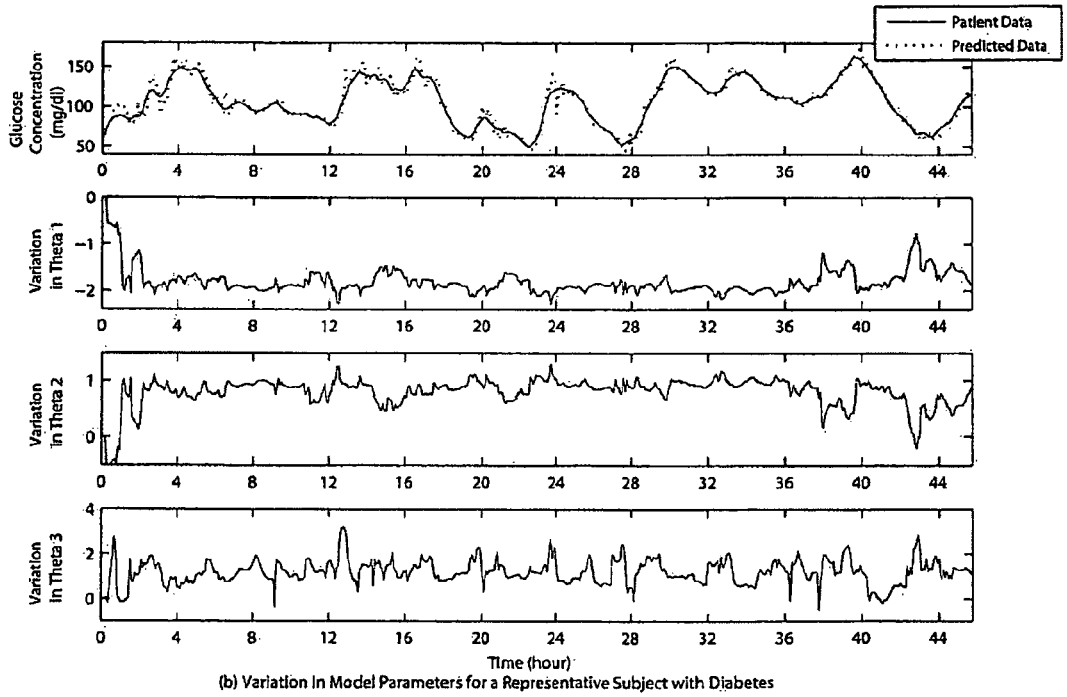
(b) Variation in Model Parameters for a Representative Subject with Diabetes
FIG. 9

AUTOMATIC INSULIN PUMPS USING RECURSIVE MULTIVARIABLE MODELS AND ADAPTIVE CONTROL ALGORITHMS

CROSS REFERENCE TO RELATED APPLICATION

This application claims the benefit of U.S. Provisional Patent Application Ser. No. 61/249,128, filed on 6 Oct. 2009. The co-pending Provisional patent application is hereby incorporated by reference herein in its entirety and is made a part hereof, including but not limited to those portions which specifically appear hereinafter.

BACKGROUND OF THE INVENTION

This invention relates generally to insulin pumps and, more particularly, to automating insulin pumps to reduce or eliminate the need for patient inputs.

Insulin pumps currently available on the market are open-loop systems that are controlled manually by the user (patient). The user computes the carbohydrate content of a meal or snack to be eaten and enters this information or the corresponding amount of necessary insulin information to the pump manually. The pump infuses this insulin. Various commercial and academic researchers are conducting research to develop automatically controlled insulin pumps. Still, a reliable fully-closed-loop insulin pump system is not commercially available. One limitation is a closed-loop control system of insulin infusion that can be easily tuned for each individual and adapt to daily variations in the patients characteristics. A control algorithm that provides tight blood glucose control in the presence of large delays associated with insulin absorption, delays between blood and subcutaneous glucose concentration changes, wide inter-subject variability of glucose-insulin dynamics and large intra-subject glycemic disturbances like meal consumption, exercise, or stress is necessary. Most systems under development are based either on proportional-integral-derivative (PID) feedback controllers or model-based predictive control strategies. To date, PID controllers have not yielded successful glucose control strategies for patients under free living conditions. Most model-based predictive control strategies use physiological models representing glucose-insulin dynamics in the body. Their performance is highly dependent on the accuracy of the process model selected to represent the true dynamics of the system. However, most of the physiological glucose-insulin models available are generally representative of an average subject under specific conditions. Nonlinearities and the large number of parameters to be identified make it difficult to tune these models for individual patients.

SUMMARY OF THE INVENTION

Patients with type 1 diabetes (T1D) usually administer insulin by multiple injections every day based on glucose measurements that they make. In recent years some patients started using insulin pumps that are adjusted manually. Patients with type 1 diabetes would like to enjoy carefree and active lifestyles, conduct physical activities and exercise programs. A closed-loop insulin pump that does not necessitate manual inputs of such as meal or physical activity information from the patient can accommodate these wishes. But the interpretation of sensor information and adaptation of the control system to significant metabolic variations is critical. This necessitates mathematical models that can represent the patient's state accurately as her/his metabolic state changes due to a wide spectrum of causes such as meals, physical activity, or stress. The invention captures glucose monitoring data and metabolic/physiological information from the patient (e.g., collected from an armband body monitoring system) and develops predictive models and closed-loop controllers for better hypoglycemia warning systems and insulin pump control systems without any additional information manually entered by the patient.

Other applications include a stand-alone hypoglycemia early warning and alarm systems. One manual insulin pump system has recently added hypoglycemia warning that stops insulin infusion when measured glucose values drop below specified limits. The system of this invention can provide early warning up to, for example, 30 minutes into the future. In testing, the prediction error 30 minutes ahead was about 6 percent when only glucose concentration values were used. The prediction error can be reduced further with the use of additional metabolic/physiological information. This glucose concentration prediction provides more time to take precautionary measures and evade the hypoglycemia episode.

The invention includes a patient-specific recursive modeling strategy. These models are developed from a patient's continuous glucose monitoring (CGM) device data by using time-series model identification techniques. The invention includes an adaptive model-based control strategy for blood glucose regulation that can dynamically respond to unpredicted glycemic variations due to physiological or external perturbations. The adaptability of the controller of this invention is further assured with subject-specific recursive linear models developed from a patient's CGM data. One important feature of the controller is the exclusive use of glucose concentration information collected from the sensor and the previous values of insulin infusion flow rates, and the elimination of the use of any manual information such as meal information. The model is desirably recursively updated at each sampling time to dynamically capture the subject's glucose variation. The recursive modeling strategy of this invention is integrated with a change detection method to ensure faster response and convergence of model parameters in presence of disturbances. The glucose prediction strategy of this invention is incorporated into an adaptive model-based control algorithm for closing the glucose control loop. Insulin (manipulated variable) absorption into the bloodstream and time-lag between subcutaneous (measured variable) and blood glucose (controlled variable) concentrations introduce large delays to the system. Therefore, time-delay compensators are included to the proposed closed-loop algorithm. The adaptability of the controller is assured since the process-model parameters are recursively tuned at each step based on CGM sensor data collected from the patient. Generalized predictive control (GPC) is used for control law computations.

The invention enhances the information from the patient by integrating CGM data with metabolic/physiological information collected from a body monitoring system and the insulin infusion rate from the pump, and developing multivariable recursive time series models and closed-loop controllers for better hypoglycemia warning systems and insulin pump control systems. This invention will provide patient-specific therapy for management of diabetes and allow significantly more freedom to patients during their daily lives.

A general object of the invention can be attained, at least in part, through a device for monitoring or treating patient glucose levels. The device includes a glucose sensor for measuring a glucose level of a patient, a physiological status monitoring system for measuring at least one physical or metabolic variable of the patient, and an automatic controller in communication with the glucose sensor and the physiological status monitoring system. The controller includes a prediction module for automatically predicting a future glucose level using data measured by the glucose sensor and the physiological sensor.

The invention further includes a method of predicting glucose levels in a patient. The method includes periodically measuring a glucose level in the patient to obtain actual glucose measurements; monitoring for physiological signals of the patient to obtain measured physiological signals or derived physiological variables; modeling a glucose concentration of the patient as a function of the actual glucose measurements and the physiological signals; and estimating future glucose levels for the patient from the model of the glucose concentration of the patient.

Signals from a CGM system will provide glucose concentration information. Physiological signals collected from a body monitoring system will provide the metabolic/physiological information. Insulin flow rates from the pump will provide previous values of the insulin flow rates. These data enable the development of multiple-input (measured glucose concentration, insulin flow rate, and metabolic/physiological information) single-output (predicted glucose concentration) models for early hypoglycemia warning and a closed-loop control system. The predicted glucose concentration will be compared with the desired glucose concentration value and the difference between these values will be used by the controller. Adaptive controllers such as generalized predictive controllers (GPC) and self-tuning regulators can be used for regulating the blood glucose level by manipulating the insulin infusion rate.

Other objects and advantages will be apparent to those skilled in the art from the following detailed description taken in conjunction with the appended claims and drawings.

BRIEF DESCRIPTION OF THE DRAWINGS

FIG. 4 includes graphs of the prediction of blood glucose with time-invariant models for a representative (a) Healthy Subject, (b) Glucose-Intolerant Subject, and (c) Subject with Type 2 Diabetes for Group A of one of the examples, with a PH of two time steps.

FIG. 5 includes a table summarizing prediction performances for several PH (prediction horizon, PH=1: 5 minutes, PH=6: 30 minutes) values using time-invariant models: (a) SSGPE values and (b) RAD values.

FIG. 6 includes graphs of glucose prediction results with the recursive algorithm for a representative (a) Healthy Subject and (b) Subject with Type 2 Diabetes for Group B of one of the examples.

FIG. 7 includes a table summarizing prediction performances using the recursive algorithm with and without the change detection strategy: (a) SSGPE Values and (b) RAD Values.

FIG. 8 includes a table summarizing the Error Matrix of CG-EGA for predicted glucose values with PH=6 of Group B of one of the examples: (A) Healthy Subgroup and (B) Type 2 Diabetes Subgroup FIG. 9 includes graphs showing variation in model parameters for a representative (a) Healthy Subject and (b) Subject with Type 2 Diabetes for study group B of one of the examples. Predicted glucose concentrations are for a PH of six time steps. Representative subjects are the same as in FIG. 6.

DETAILED DESCRIPTION OF EMBODIMENTS OF THE INVENTION

The invention includes an automatic insulin pump control and early hypoglycemia alarm systems based on simple recursive models that are updated, for example, at each sampling time to adapt to the current state of the patient. The recursive patient-specific dynamic models use subcutaneous glucose measurements, infusion flow rates from the pump and physiological data that report metabolic information, physical activity and stress to provide accurate predictions of blood glucose concentrations and do not need any manual information such as meal contents entered by the patient. These models predict future glucose concentrations for use in early warning systems for hypoglycemia predictions and alarms and in adaptive controllers that manipulate automatically the insulin infusion rate.

The present invention provides a device for monitoring or treating patient glucose levels. The device is schematically shown in FIG. 1, and can be implemented through or including, without limitation, currently known devices such as armband sensors, glucose sensors, and insulin pumps, modified as necessary to operate according to the modeling strategy of this invention.

Figure 1:
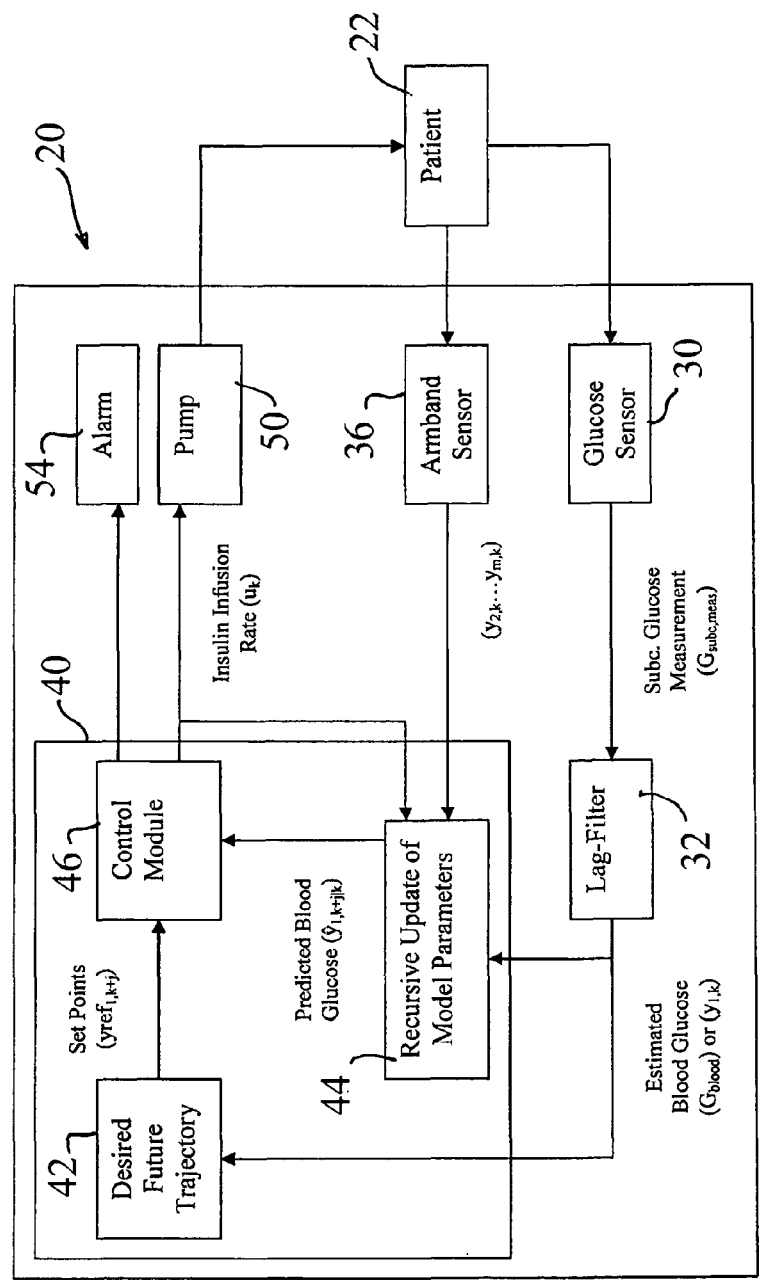
FIG. 1 is a block diagram of an automated closed-loop blood glucose monitoring/treating device according to one embodiment of this invention.

FIG. 1 illustrates components of device 20 for monitoring or treating glucose levels in a patient 22. The broader aspects of this invention are not intended to be limited to any particular implementation, and are thus shown schematically in FIG. 1. For example, the device 20 can be implemented as a single device including all components contained within a single housing, but is more practically implemented at this time through a combination of components where at least one component is separately housed and communicates with the one or more of the other components, such as wirelessly.

The device 20 includes a glucose sensor 30 for measuring a glucose level of the patient 22. The glucose sensor 30 desirably is embodied as a continuous blood glucose monitor (CGM) that determines blood glucose levels of interstitial fluids on a continuous basis, such as every few minutes. A typical CGM includes a disposable glucose sensor that is placed just under the skin, which is worn for a period of time until replacement, and a non-implanted electronic receiver component worn by the user. In one embodiment of this invention, the receiver components can be integrally combined with other components of this invention, such as are discussed below. The glucose sensor 30 desirably includes a power source that is rechargeable without a wired connection and computational capabilities, such as a data processor and recordable medium (e.g., flash memory) to implement the necessary modeling algorithms of this invention.

Glucose levels in interstitial fluid temporally lag behind blood glucose values, generally understood to be about five minutes behind. This lag can create issues during times of rapidly changing glucose levels. In the embodiment illustrated in FIG. 1, the device 20 includes a measurement delay filter compensator 32 to address this glucose reading lag time. The filter compensator 32 takes the subcutaneous glucose measurement and determines an estimated blood glucose level. The filter compensator can be implemented within the glucose sensor 30, or within another component of device 20 depending on need.

The device 20 also includes a physiological status monitoring system 36 for measuring at least one physical or metabolic variable of the patient 22. Examples of physical or metabolic variables that can be monitored by the physiological status monitoring system 36 include, without limitation, movement (e.g., incorporating an accelerometer), skin temperature, dissipated heat from the body, galvanic skin response, or combinations thereof. The system 36 includes the necessary sensors for detecting the above mentioned variables. The system 36 can also include a software module on a recordable medium for deriving at least one variable selected from sleep, total energy expenditure, stress, physical activity, or combinations thereof.

The physiological status monitoring system 36 can be implemented according to need. In one embodiment of this invention, the physiological status monitoring system 36 is implemented as an armband monitoring system worn by the patient 22. The armband desirably wirelessly communicates with other components of the device, such as using wireless local area network technologies or other radio frequencies. One exemplary armband monitor that can be used and/or modified for use in the device 20 is available from Bodymedia, Inc., and sold under the name SENSEWEAR.

The device 20 further includes an automatic controller 40 in communication with the glucose sensor 30 and the physiological status monitoring system 36. The controller includes a prediction module 42 for automatically predicting a future glucose level using data measured by the glucose sensor and the physiological sensor. The controller 40 includes a processor in combination with a recordable medium for implementing the control model according to this invention. The recordable medium stores the data measured by the glucose sensor and the physiological sensor, and the prediction module 42 predicts the future blood glucose level using at least a portion of the stored measured information by the glucose sensor and the physiological sensor.

In one embodiment, the prediction module includes an algorithm for predicting future glucose concentration values at or between 5 to 30 minutes into the future. The prediction module desirably includes a recursive model for predicting the future glucose level using data measured by the glucose sensor and the physiological sensor. The controller 40 also desirably includes an update module 44 for continuously updating the parameters of the recursive modeling, based upon the measurements of the sensors and the amount of insulin prescribed in response to the future glucose prediction.

The controller 40 includes a control module 46 that acts upon the predicted blood glucose levels by implementing an insulin pump 50. The controller 40 provides an insulin infusion rate to the insulin pump 50 as a function of the predicted future glucose level. The device 20 can also include an alarm 54 for alerting the patient of an unsafe current or future glucose level.

Any suitable insulin pump and alarm mechanism can be used in this invention. The insulin pump desirably includes an insulin reservoir that can be refilled without removing the entire pump device. As it can be desirable to limit the number of separate components, several of the components can be implemented in a single integrated device. In one embodiment of this invention, more than one, or all, of the glucose sensor, controller, pump, and alarm can be implemented in a single device housing. Integral components can communicate by wired connections, whereas separately housing components, such as any armband sensor(s), can communicate wirelessly through know wireless technologies.

The glucose monitoring and/or treating device of this invention is preferably a closed-loop system that does not requiring user inputs for either predicting patient glucose levels or, desirably, for operating the insulin pump. In one embodiment of this invention, the device implements a method of predicting glucose levels in a patient. The device periodically measures a glucose level in the patient to obtain actual glucose measurements, which can be modified as needed to account for any lags due to the type of sensor mechanism. The device further monitors for physiological signals of the patient to obtain measured physiological signals or derived physiological variables. The device models a glucose concentration of the patient as a function of the actual glucose measurements and the physiological signals. Using the patient model, the device estimates a future glucose level for the patient from the model of the glucose metabolism of the patient, and can provide insulin according to the estimation.

As discussed above, the patient model can be updated in view of new information from the patient measurements. In one embodiment of this invention, the device determines changes in glucose metabolism model parameters and modifies the glucose metabolism modeling in view of the new parameters. In one embodiment, such as where the modeling includes multivariate recursive time series modeling, the model is automatically recursively updated with each of the actual glucose measurements. A determined difference between the estimated future glucose level for a timeframe and an actual glucose measurement for that timeframe can be a trigger and used for modifying the model of the glucose metabolism. The glucose metabolism model can be established and updated by analysis of the stored actual measurements for a timeframe and the corresponding physiological data sampled during that timeframe.

The invention includes a recursive multivariate dynamic model that describes glucose homeostasis in the patient body and provides hypoglycemia, warning systems and closed-loop automatic adaptive controllers to regulate blood glucose levels by manipulating insulin infusion rates from an automatically controlled pump. Signals from the continuous glucose monitoring device and the multi-sensor body monitor (e.g., armband) are used for initial model development. The models developed are subject-specific (they can handle inter- and intra-subject variabilities of glucose metabolism) and desirably do not require any manual inputs from the subject (they function in fully automated form).

Algorithm for Early Hypoglycemia Alarms

Avoiding hypoglycemia while keeping glucose within the narrow normoglycemic range (70-120 mg/dl) is a major challenge for patients with diabetes. Glucose concentrations below 40 mg/dl can cause severe impairment in the nervous system that has the potential to lead to seizure, diabetic coma, and eventually death. Patients will benefit from an early alarm that predicts a hypoglycemic episode before it occurs, allowing enough time to the patient to take the necessary precaution (e.g., food ingestion or insulin administration).

Time-series techniques have been utilized to develop the multivariate model called VARMA (Vector Autoregressive Moving Average) that relates several variables observed simultaneously over time. Suppose that m related time-series variables are considered, $y_{1,k}, y_{2,k}, \ldots, y_{m,k}$, where k denotes the sampling instant, $y_{1,k}$ represents the glucose measurements from the CGM sensor, and the remaining variables $(y_{2,k}, \ldots, y_{m,k})$ are the physiological signals from the physiological status monitoring system such as energy expenditure, longitudinal and transverse acceleration, near body temperature, etc.

Using vector (underlined) and matrix (double underlined) notations, the VARMA model at time k can be written as:

$$\underline{y}_k = \sum_{i=1}^{n_A} \underline{\underline{A}}_{i,k} \underline{y}_{k-i} + \sum_{i=1}^{n_C} \underline{\underline{C}}_{i,k} \underline{e}_{k-i} + \underline{e}_k \quad (1)$$

where the system output and the residuals vectors of m variables are $\underline{y}_k = [y_{1k}\ y_{2k}\ \ldots\ y_{mk}]^T$ and $\underline{e}_k = [e_{1k}\ e_{2k}\ \ldots\ e_{mk}]^T$, respectively. $n_A$ and $n_C$ describes the model order (windows of past observations used for prediction). $\underline{\underline{A}}_{i,k}$ and $\underline{\underline{C}}_{i,k}$ are the m×m matrices consisting of model parameters for the outputs and residuals at sampling instant k:

$$\underline{\underline{A}}_{i,k} = \begin{bmatrix} a_{11,i} & \cdots & a_{1m,i} \\ \vdots & \ddots & \vdots \\ a_{m1,i} & \cdots & a_{mm,i} \end{bmatrix}_k \text{ and } \underline{\underline{C}}_{i,k} = \begin{bmatrix} c_{11,i} & \cdots & c_{1m,i} \\ \vdots & \ddots & \vdots \\ c_{m1,i} & \cdots & c_{mm,i} \end{bmatrix}_k \quad (2)$$

Equation (1) can also be expressed in terms of matrix polynomials:

$$\underline{\underline{A}}_k(q^{-1})\underline{y}_k = \underline{\underline{C}}_k(q^{-1})\underline{e}_k \quad (3)$$

where $$\underline{\underline{A}}_k(q^{-1}) = \underline{\underline{I}}_{m \times m} - \underline{\underline{A}}_{1,k}q^{-1} - \ldots - \underline{\underline{A}}_{n_A,k}q^{-n_A} \quad (4)$$

$$\underline{\underline{C}}_k(q^{-1}) = \underline{\underline{I}}_{m \times m} + \underline{\underline{C}}_{1,k}q^{-1} + \ldots + \underline{\underline{C}}_{n_A,k}q^{-n_A} \quad (5)$$

and $q^{-1}$ is the back-shift operator (e.g. $\underline{y}_k q^{-i} = \underline{y}_{k-i}$).

The model described in equation (3) estimates the current output ($\underline{y}_k$) using the previous measurements ($\underline{y}_{k-1} \cdots \underline{y}_{k-n_A}$) from the sensors, and $\underline{e}_k$ represents the modeling error between the estimated ($\hat{\underline{y}}_k$) and actual measured ($\underline{y}_k$) variables. The model parameters which are contained in the matrix polynomials $\underline{\underline{A}}_k(q^{-1})$ and $\underline{\underline{C}}_k(q^{-1})$ are time-varying and are recursively identified at each sampling time as new data become available to include the most recent glucose dynamics information. On-line identification is achieved with weighted recursive least squares (RLS) method:

$$\underline{\hat{\theta}}_k = \underline{\hat{\theta}}_{k-1} + \underline{K}_k \left\{ \underline{y}_k - \underline{\varphi}_k^T \underline{\hat{\theta}}_{k-1} \right\}, \quad (6)$$

$$\underline{K}_k = \frac{\underline{\underline{P}}_{k-1} \underline{\varphi}_k}{\lambda + \underline{\varphi}_k^T \underline{\underline{P}}_{k-1} \underline{\varphi}_k}, \quad (7)$$

$$\underline{\underline{P}}_k = \frac{1}{\lambda}\left[\underline{\underline{P}}_{k-1} - \frac{\underline{\underline{P}}_{k-1}\underline{\varphi}_k \underline{\varphi}_k^T \underline{\underline{P}}_{k-1}}{\lambda + \underline{\varphi}_k^T \underline{\underline{P}}_{k-1} \underline{\varphi}_k}\right]. \quad (8)$$

In equation (6), the estimated model parameters are denoted by $\hat{\theta}_k$. The matrices $\underline{K}_k$ and $\underline{\underline{P}}_k$ represent the estimator gain and estimate of error variance respectively, whereas $\underline{\varphi}_k$ is the matrix containing the past observations $(\underline{d}_{k-1}, \ldots, \underline{y}_{k-n_A}, \underline{e}_{k-1}, \ldots, \underline{e}_{k-n_C})$. $\lambda$ is the forgetting factor ($0 < \lambda \leq 1$) that assigns relative weights on past observations for model development. When $\lambda = 1$, all observations are equally weighted (infinite memory). Small values of $\lambda$ give more weight on recent observations (short memory).

The RLS with a constant $\lambda$ will normally provide sufficient model tracking unless the system deviates from its steady state operating conditions. However, daily glucose excursions include large transition periods (e.g. after a meal consumption). Therefore, a variable $\lambda$ is used which takes a small value during transition periods (change detected) and a large value during fasting conditions. The mechanism for varying $\lambda$ is implemented with a change detection strategy integrated to the RLS algorithm that monitors the variation in the model parameters. When the algorithm detects a change in parameters, the value of forgetting factor in the RLS is reduced. A small $\lambda$ ensures that the new information about the change in the system dynamics is quickly collected and the old information is discarded. The proposed change detection method is described by null and alternative hypotheses given by:

$$H_0: E(\underline{\theta}_k) = \underline{\Theta}_N, \text{ for } N < k < N + N_W$$

$$H_1: E(\underline{\theta}_k) \neq \underline{\Theta}_N, \text{ for } N < k < N + N_W \quad (9)$$

$E(\theta_k)$ describes the expected value of parameter estimates at kth sampling instant, and $\Theta_N$ is the expected value computed using the data until time instant N. To avoid changes due to non-persistent abnormalities in the data such as sensor noise, the value of $\lambda$ is not reduced at the first instant of change detection. Instead, consistency of the change for several time steps (window size, $N_W$) is assured first. When a persistent change with the duration of the window size is detected, $\lambda$ is reduced to a smaller value and $\Theta_N$ is replaced with its new estimate.

After identification of the model parameters at each step using the RLS (6)-(8) and the change detection method (9), the model in equation (3) (now with known parameters) is appended n-steps into the future to predict the future excursion of output variables ($\hat{\underline{y}}_{k+n|k}; \hat{\theta}_k$) using only the data available at current sampling time k:

$$\hat{y}_{k+n|k;\hat{\theta}_k} = \frac{\underline{G}_k(q^{-1})}{\underline{C}_k(q^{-1})}\underline{y}_k. \tag{10}$$

The matrix polynomial $C_k(q^{-1})$ is given by equation (5), whereas the polynomial $\overline{G}_k(q^{-1})$ has the order equal to (g−1) with $g=\max(n_A, n_C-n+1, 1)$ and is uniquely defined by following Diophantine equation:

$$\underline{C}_k(q^{-1}) = \underline{A}_k(q^{-1}) + q^{-n}\underline{G}_k(q^{-1}), \tag{11}$$

In (11), $A_k(q^{-1})$ is described by (4) and the polynomial $F_k(q^{-1})$ has order of (n−1).

Using (10), the n-steps-ahead predicted glucose value ($\hat{y}_{1,k+n|k;\hat{\theta}_k}$) which is the first element of the vector $\hat{y}_{k+n|k;\hat{\theta}_k}$ is used to issue early hypoglycemia alarms according to one embodiment of this invention. When the predicted glucose level ($\hat{y}_{k+n|k;\hat{\theta}_k}$) is below the assigned threshold (e.g., 60 mg/dl) value for hypoglycemia, then an alarm is issued to warn the patient that hypoglycemia will be experienced n-steps-ahead from the current time.

In summary, the model developed is subject-specific and dynamically captures inter- or intra-subject variability. Parameters are identified recursively using the weighted RLS. A variable forgetting factor is implemented with a change detection strategy which aims to achieve good data tracking not only during slow frequency changes in glucose dynamics but also during drastic and sudden variations. The modeling algorithm estimates future glucose and physiological signal levels using recent history of measurements only, and does not require any prior experimental data, tuning for each subject, or disturbance information. Therefore, it can easily be implemented for any subject using a CGM sensor and a multi-sensor body monitor (armband).

Some of the CGM sensors available in the market provide a hypoglycemic alarm when the measured glucose decreases below a user specified threshold. However, patients will benefit more from an early alarm that predicts the hypoglycemic episode before it occurs providing time for corrective action to be taken. A few of the available CGM sensors provide such early alarms generally by linear extrapolation of the rate of change of glucose concentration into the future (e.g., Weinstein R L, et al., "Accuracy of the 5-day FreeStyle Navigator Continuous Glucose Monitoring System: comparison with frequent laboratory reference measurements." Diabetes Care 2007; 30(5):1125-1130). Differently, the algorithm according to this invention predicts future glucose concentrations using more reliable subject-specific and dynamic models that utilize not only glucose measurement data but also physiological signals from an armband.

Algorithm for Fully Automated Closed-Loop Blood Glucose Regulation

Patients with diabetes, especially with type 1 diabetes who have no endogenous insulin, control their blood glucose concentrations by administering exogenous insulin and balancing their diet. With current therapy, insulin is delivered through multiple daily injections (3 to 5 injections, usually taken before meals) or a manually controlled subcutaneous insulin pump. Patients adjust their bolus (meal-related) insulin dose based on their pre-meal blood glucose test, estimated carbohydrate content of the meal and planned post-meal activity levels. Success rate at achieving normoglycemia with current insulin therapies has been very low, and patients may experience prolonged hyperglycemic or hypoglycemic episodes. The main reason is that patients have difficulty in predicting future glucose concentrations and therefore determining the required insulin amount with the changing daily life conditions (e.g., diet, exercise, stress, or illness) and the high intra-patient variation in glucose metabolism.

The closed-loop device and method of this invention are designed to replace the current insulin injections or manual insulin pumps with a fully-automated system that eliminates any patient intervention and can adjust to any individual's need. The closed-loop algorithm for blood glucose regulation according to this invention provides effective control to a wide range of inter-/intra-subject variability of glucose-insulin dynamics. The algorithm also accounts for delays associated with insulin absorption or time-lag between blood and subcutaneous glucose concentrations.

FIG. 1, discussed above, illustrates a schematic representation of a proposed adaptive closed-loop strategy. Integration of a subcutaneous CGM sensor 30, a multi-sensor body monitor 36 (armband or similar device) and a continuous subcutaneous insulin delivery system 50 is provided. A measurement delay compensator 32 is introduced to estimate the current blood glucose concentration ($G_{blood}$) from subcutaneous glucose measurements ($G_{subc,meas}$) that accounts for the time-lag between the two. Then, the estimated blood glucose concentration, the physiological signals from the armband and the insulin infusion rate are utilized to develop the multivariate subject-specific model whose parameters are recursively identified at each sampling step. The signals from the two sensors (CGM device 30 and armband 36) constitute the outputs of the model, whereas the insulin infusion rate is the input. The model developed is next used for predicting future glucose excursion of the subject which is inputted to the adaptive model-based controller system. The controller 40 also can receive or provide a reference (desired) future blood glucose excursion that is a function of current blood glucose concentration. The device also desirably contains an insulin transport compensator that accounts for the time-delay introduced to insulin-action due the subcutaneous insulin absorption.

For the closed-loop glucose control system, the VARMA model in (3) is extended to include the insulin infusion rate (input-term):

$$\underline{A}_k(q^{-1})\underline{y}_k = q^{-d}\underline{B}_k(q^{-1})u_k + \underline{C}_k(q^{-1})\underline{e}_k \tag{12}$$

which is known as VARMAX (Vector Autoregressive Moving Average with Exogenous Variables) model. In (12), the $q^{-d}$ term introduces d-steps of delay in insulin action. The matrix polynomials $A_k(q^{-1})$ and $C_k(q^{-1})$ are given by (4) and (5) respectively. Similarly, the polynomial $B_k(q^{-1})$ is defined as:

$$B_k(q^{-1}) = b_{0,k} + b_{1,k}q^{-1} + \ldots + b_{n_B,k}q^{-n_B}. \tag{13}$$

The parameters of the VARMAX model of (12) are recursively identified by RLS and change detection methods described by (6)-(9). The parameter vector ($\hat{\theta}_k$) of (6) is appended by $n_B$ parameters to include the $b_{0,k} \ldots b_{n_B,k}$.

Similar to equation (10), j-steps-ahead predicted signal values ($\hat{y}_{k+j|k;\hat{\theta}_k}$) are given by:

$$\hat{y}_{k+j|k;\hat{\theta}_k} = \frac{1}{\underline{C}_k(q^{-1})} \cdot [\underline{G}_k(q^{-1})\underline{y}_k + B_k(q^{-1})\underline{F}_k(q^{-1})u_k] \tag{14}$$

Reference glucose trajectory is a time-varying function of the current blood glucose concentration. Glucose concentration of 80 mg/dl is the ultimate target. For glucose measurements below the target value, an exponentially increasing trajectory is tracked to ensure faster recovery from hypoglycemic conditions. On the other hand, for hyperglycemic glucose readings (>160 mg/dl) a linearly decreasing trajectory with a rate of 10 mg/dl/step is preferred. This rate is reduced to 5 mg/dl/step for glucose measurements within the 160-80 mg/dl range. The objective is to avoid any sudden decrease in glucose concentrations that can be caused by aggressively high insulin infusion rates, and to have a faster response during hypoglycemic conditions.

Finally, the controller uses the generalized predictive control (GPC) strategy to compute the optimum insulin infusion rate for the subject. The insulin infusion rate ($u_k$) is determined by solving an optimization problem that minimizes the deviation of predicted blood glucose values ($\hat{y}_{1,k+j|k}$) from a reference glucose trajectory ($y_{ref,k+j}$):

$$J(N_y, N_u) = \sum_{j=1}^{N_y} \underline{q}[\hat{y}_{k+j|k} - yref_{k+j}]^2 + \sum_{j=1}^{N_u} r[\Delta u_{k+j-1}]^2. \quad (15)$$

where $\Delta u_k$ is the incremental control input at kth sampling step, and $\Delta u_k = u_k - u_{k-1}$. Output prediction horizon ($N_y$), control horizon ($N_u$), and weights on output deviation and incremental input (q and r respectively) are the controller design parameters. $N_u \leq N_y$ is used and for $i \geq N_u$, $\Delta u_{k+i} = 0$ is assumed.

The minimization of the cost function (15) gives the optimal control action (insulin infusion rate). This requires the estimation of j-step-ahead blood glucose predictions $\hat{y}_{1,k+j|k}$ which are given as the first element of vector $\hat{y}_{k+j|k:\hat{\theta}_k}$ in equation (14). From (14), $\hat{y}_{1,k+j|k}$ can be expressed by:

$$\hat{y}_{1,k+j|k} = G_j \Delta u_{k+j-1} + \Gamma_j \Delta u^f_{k-1} F_j y_{1,k}^f. \quad (16)$$

which is a function of future control actions (first term on the right-hand-side), past insulin infusion rates (second term on the right-hand-side) and past blood glucose levels (third term on the right-hand-side). Polynomials $G_j$ and $\Gamma_j$ are defined from a second Diophantine equation ($H_j = G_j \tilde{C} + g^{-j} \Gamma_j$ with $H_j = E_j B$). Using (16), future estimations over the entire prediction horizon can then be expressed in a vector notation as:

$$\underline{\hat{y}}_1 = \underline{G}\underline{\tilde{u}} + \underline{f} \quad (17)$$

where $$\underline{\hat{y}}_1 = [\hat{y}_{k+1|k} \hat{y}_{k+2|k} \ldots \hat{y}_{k+N_y|k}]^T, \quad (18)$$

$$\underline{\tilde{u}} = [\Delta u_k \Delta u_{k+1} \ldots \Delta u_{k+N_u-1}]^T. \quad (19)$$

Vector f is defined as free response predictions and corresponds to last two terms in (16). Substituting (17) into (15), the cost function is solved to give the vector of future optimum control actions:

$$\underline{\tilde{u}} = (\underline{G}^T \underline{G} + \beta I)^{-1} \underline{G}^T (\underline{yref} - \underline{f}), \quad (20)$$

with $\beta = r/q$. Only the first element of the input sequence is implemented, and at the next sampling step, the optimization procedure is repeated.

The invention thus provides a control algorithm for fully automated closed-loop insulin therapy. The model-based controller utilizes a subject-specific modeling algorithm and the adaptability of the controller is provided with on-line identification of the model at each step. The focus is on the route with the longest delay (subcutaneous) for both glucose sensing and insulin delivery, and delay compensators are introduced in order to account for the time-lag between subcutaneous and blood glucose concentrations and delay in insulin action. While developed by keeping in mind the challenges with subcutaneous-subcutaneous glucose-insulin route, explicitly expressed time-delay compensators makes the application of the proposed algorithm straightforward to any other glucose-insulin route (it requires the adjustment of time-delay values only). The controller description is given for GPC strategy; however, the algorithm can be applied with any other model-based control methods.

The algorithm generally does not require any physiological representation of glucose-insulin dynamics, additional disturbance modeling, manual inputs by the patient, or prior experimental data for subject-specific tuning. This approach has the capacity to significantly improve management with diabetes by providing total freedom in daily lives of the patients while reducing the burden of frequent blood glucose testing and insulin adjustments; and therefore reducing the development of complications and improving quality of life for patients.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

Tight control of glucose levels is important for the management of diabetes. Large swings in glucose can be detrimental to the patient, increasing diabetic complications such as retinopathy, neuropathy, and nephropathy. It is difficult for people with diabetes to predict their future glucose values in order to adjust the necessary amount of insulin or their eating habits, since the glucose-insulin system is very complex. This invention provides subject-specific empirical models that model the dynamics of glucose in the blood and predict future glucose levels. Models can be used for hypo-/hyperglycemic alarms and eventually an artificial pancreas. For this example, twenty-one days of data from a CGM device and SENSEWEAR armband from one subject with type 2 diabetes were used to develop and validate various orders of autoregressive models with exogenous inputs (ARX). The parameters for the model were identified non-recursively as well as recursively. The accuracy of the model predictions is evaluated by determining the absolute average error (AAE). Results show that a linear time-series model is a reliable method for predicting future glucose levels.

Data used in this study was collected from one subject with type 2 diabetes over twenty full days (3 am to 3 am). A Medtronic MiniMed Continuous Glucose Monitor, MMT-7012, was used to gather the glucose data. This device measures subcutaneous glucose concentrations every five minutes. For the physiological information, the BodyMedia SENSEWEAR PRO body monitoring system was used. For this example, the following signals were used: near-body temperature, energy expenditure, galvanic skin response, heat flux, average longitudinal acceleration, transverse acceleration peaks, and transverse acceleration mean of absolute difference. The last three variables are measured by a two-axis accelerometer in order to identify the subject's activities. The SENSEWEAR armband takes measurements every minute, so the data was trimmed to include the data points at the same time as those from the glucose monitor. The subject was allowed to live normally, as no requirements were set as to food consumption or exercise.

Time-series models were used to describe the dynamics of glucose. From the various structures of time-series models, the autoregressive with exogenous input (ARX) model is used:

$$g(t) = -a_1 g(t-1) - a_2 g(t-2) + b_1 n(t-6) + b_2 h(t-1) + b_3 s(t-8) + b_4 p(t-6) + e(t)$$

g=Blood glucose concentration n=Near-body temperature
h=Heat flux s=Galvanic Skin Response
p=Transverse acceleration peaks e=Error
t=Current time step a and b are parameters to be identified Two methods, Least Squares (LS) and Recursive Least Squares (RLS), were used to identify the parameters of the time-series models. LS was used for the non-recursive case, where the model parameters were held constant. On the other hand, RLS was used to update the model parameters at each sampling step.

The accuracy of the models was evaluated using the average absolute error (AAE):

$$AAE = \frac{1}{N}\sum_{i=1}^{N}|y(t) - \hat{y}(t|t-k)|$$

y(t)=Measured glucose concentration from the CGM device
ŷ(t|t−k)=k-step ahead predicted glucose concentration using the ARX model Table 1 shows the average prediction errors for 4-input recursive model through 6-steps ahead for all 20 days

TABLE 1

| | k-step | | | | | |
|---|---|---|---|---|---|---|
| | 1 | 2 | 3 | 4 | 5 | 6 |
| AAE | 1.28 | 2.42 | 3.54 | 4.64 | 5.71 | 6.74 |

Figure 2:
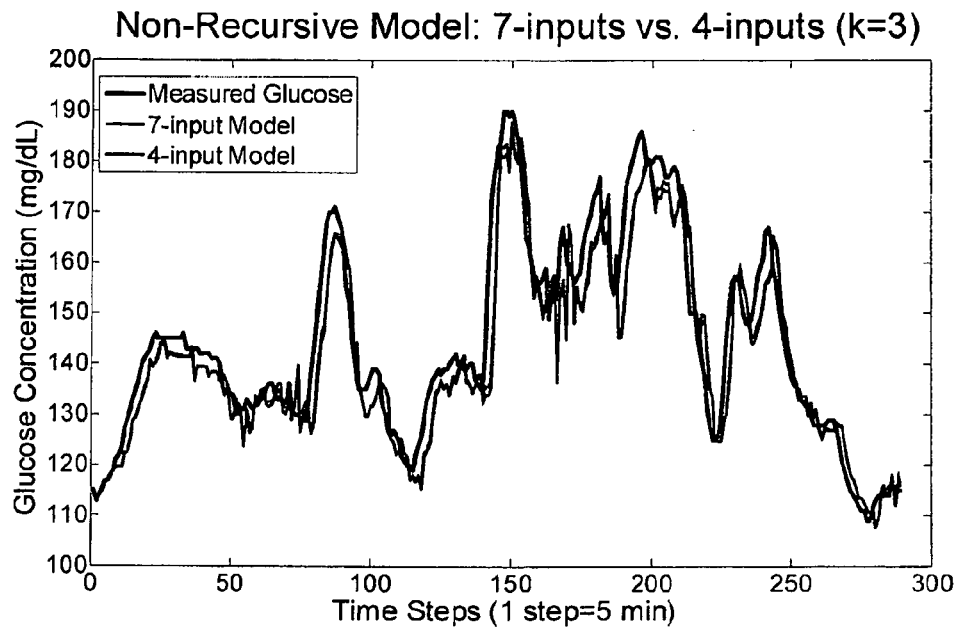
FIGS. 2 and 3 are graphs produced during testing of examples of the invention.

Model parameters were generated using the LS method. All seven physiological inputs were used. Then the number of inputs was reduced to four (near body temperature, heat flux, galvanic skin response, and transverse acceleration peaks) in order to reduce computational load without significant reduction in performance. FIG. 2 shows a plot of the seven inputs versus the four inputs.

Figure 3:
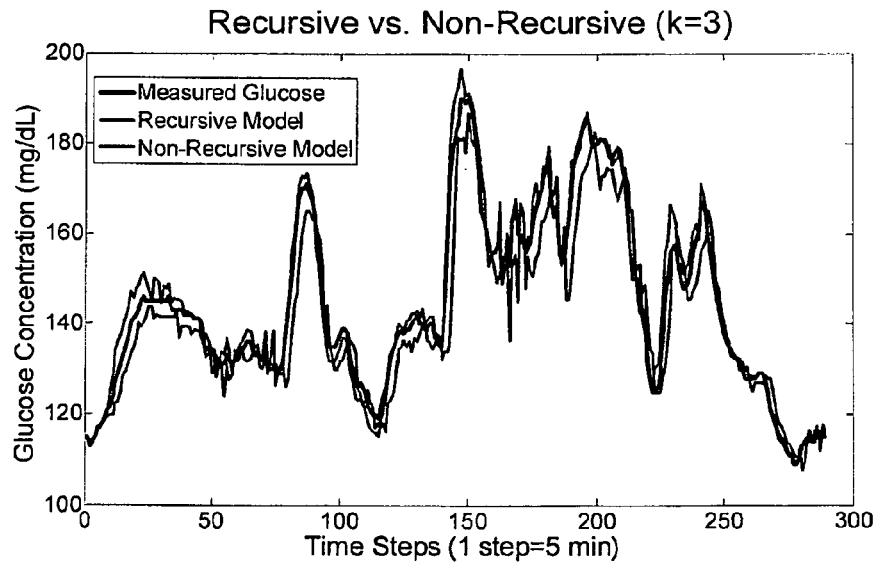

The model with changing parameters is implemented using the RLS method. Recursive models are better than non-recursive models for modeling complex nonlinear systems because the parameters can adapt at each step in response to the changes in the system. FIG. 3 is a plot of recursive versus non-recursive models.

The comprehensive 7-input model was reduced to 4-inputs without sacrificing performance. Overall, this example shows that the non-recursive case is sufficient for predicting the immediate future (1- and 2-steps ahead).

Blood Glucose Regulation with an Adaptive Model-Based Control Algorithm

The performance of model-based control algorithms is highly dependent on the accuracy of the process-model used to represent the true dynamics of the system. Time-series analysis was utilized to develop linear and low-order autoregressive moving-average models (ARMA) from patient's own continuous glucose monitoring data. At each sampling step, the model parameters were recursively tuned using the weighted RLS method. The RLS algorithm was further integrated with a change detection method to dynamically capture the unpredicted glucose fluctuations due to physiological or external perturbations and to provide a faster response under such conditions. The glucose prediction strategy was then integrated with adaptive model-based control methods for closing the glucose control loop for patients with diabetes.

Depending on the site of glucose measurement and/or insulin delivery, one of the major challenges of the closed-loop glucose regulation is the variable time-delay introduced to the system due to insulin absorption into the bloodstream and time-lag between subcutaneous glucose and blood glucose concentrations. Subcutaneous space appears to be the minimally invasive site and therefore is the most preferred site by CGM devices and insulin pumps currently available in the market. This invention focuses on the most delayed site (subcutaneous) for both glucose measurements and insulin administration. To cope with delays associated with insulin absorption, a Smith predictor-like structure was introduced to the closed-loop algorithm. Even though almost all of the available CGM sensors monitor glucose in the subcutaneous interstitial fluid rather than blood, management of diabetes is still defined in terms of blood glucose (not subcutaneous) by clinicians and therefore the standard choice for control performance is still the blood glucose regulation. Therefore, a lag-filter was introduced to account for the time-lag between subcutaneous and blood glucose to the closed-loop structure.

In summary, variations in glucose-insulin dynamics were monitored by online identification of the model. At each step with the new coming subcutaneous glucose measurement, the current blood glucose concentration was estimated using the lag-filter. Model parameters were updated, and estimation of future time course of blood glucose was performed. These parameters were then used in the model-based control algorithm for calculation of the appropriate control action (insulin infusion rate). The required insulin infusion rate was determined by solving an optimization problem that minimizes the deviation of the predicted glucose values from a reference glucose trajectory. Two well-known model-based control strategies, generalized predictive control (GPC) and linear quadratic control (LQC) were used for control-law calculations, and were modified to include a delay compensator (Smith predictor-like structure) associated with insulin absorption and a time-varying reference glucose trajectory.

Assuming subcutaneous glucose measurements, the closed-loop performance was evaluated on a simulated patient with type 1 diabetes and results were reported for subcutaneous delivery of rapid-acting insulin. The algorithm was able to keep blood glucose concentrations within normoglycemic range in presence of multiple-meal consumptions with simultaneous physiological glucose variations (e.g. changes in insulin sensitivity). The proposed closed-loop algorithm for blood glucose regulation provided robust control to a wide range of inter-/intra-subject variability of glucose-insulin dynamics and it further accounted for delays associated with insulin absorption or time-lag between plasma and interstitial glucose concentrations.

Blood Glucose Regulation for Patients with Type 1 Diabetes with an Augmented Self-Tuning Controller An implicit self-tuning tracker was developed to keep blood glucose concentrations close to a time-varying reference glucose trajectory. Adaptation of the controller to intra-/inter-subject variability was assured with recursive identification of patient specific time-series models derived from patient's own CGM device data. The recursive identification strategy is integrated with a change detection method to provide faster converge of model parameters. Insulin (manipulated variable) absorption into the bloodstream and time-lag between subcutaneous glucose (measured variable) and blood glucose (controlled variable) concentrations introduce large delays to the closed-loop system. The self-tuning regulator was augmented to include time-delay compensators.

The self-tuning tracker was able to keep blood glucose concentrations within desired limits (postprandial maximum glucose values below 160 mg/dl, normalization of glucose levels to 120-70 mg/dl within 2-3.5 hours after meals) for subcutaneous insulin infusion (route with largest delay). A self-tuning tracker for regulation of blood glucose concentrations has thus been developed. Including a change detection method to the recursive algorithm and integrating time-delay compensator to the controller structure, improves blood glucose control.

Glucose Prediction

In this example, two separate patient databases collected under hospitalized (disturbance-free) and normal daily life conditions were used for validation of the proposed glucose prediction algorithm. Both databases consisted of glucose concentration data collected at 5-min intervals using a CGM device. Using time-series analysis, low-order linear models were developed from the patients' own CGM data. The time-series models were integrated with recursive identification and change detection methods, which enables dynamical adaptation of the model to inter-/intra-subject variability and glycemic disturbances. Prediction performance is evaluated in terms of glucose prediction error and Clarke Error Grid analysis (CG-EGA). The results included a significant reduction in prediction errors using recursive identification of the models, and predictions were further improved with inclusion of a parameter change detection method. CG-EGA analysis results in accurate readings of 90% or more.

Two separate patient databases collected under (1) disturbance-free (hospitalized) and (2) normal daily life conditions were used. Both databases consisted of glucose concentration data collected using a CGM device. The two study procedures were reviewed and approved by the University of Illinois at Chicago Institutional Review Board. Prior to participating in the study, all subjects completed consent and HIPPA documents. Data collection took place at the University's general clinical research center.

Study Group A

This study population consisted of healthy individuals (sample size n=22, 43.50±10.4 years old, body mass index [BMI]=35.02±3.4 kg/m$^2$), glucose-intolerant subjects (n=7, age 45.00=7.0 years, BMI=34.88±4.1 kg/m$^2$), and subjects with type 2 diabetes (n=11, 47.18±5.1 years old, BMI=36.80±4.1 kg/m$^2$). Data were originally collected to investigate the effect of moderate exercise (30-min walk on a treadmill performed before breakfast at an intensity of 65% maximal oxygen consumption ($V^*O_{2_{max}}$) measured with indirect spirometry) on postprandial glucose during two separate randomized protocols (exercise and nonexercise). Subjects were hospitalized for 48 hours and were prescribed three standard meals for each day. A subject's glucose concentration was monitored with a CGM system (CGMS System Gold™, Medtronic MiniMed, Northridge, Calif.) for 48 hours. In this example, the CGMS data collected during the nonexercise protocol was used.

Study Group B

This study population consisted of subjects with type 2 diabetes (n=14, 47.93±6.1 years old, BMI=36.94±4.9 kg/m$^2$) and healthy subjects (n=8, 42.75±12.7 years old, BMI=34.66±5.8 kg/m$^2$). The database consisted of glucose concentration data collected at 5-min intervals using the CGMS System Gold monitoring device. The subjects wore the CGMS at home for 48 hours, with no additional instructions other than how to operate the monitor and calibration techniques of the device.

Recursive linear models were developed using the patient's own CGM data. Low-order linear models would be less accurate than nonlinear models for describing variations of a nonlinear system in a wide range of conditions. However, it was shown that recursive identification of the model will compensate for its simplicity and improve its accuracy.

Current or future glucose concentrations were expressed as a function of previous glucose measurements with autoregressive (AR) or autoregressive moving average (ARMA) models:

AR model: $y(t)=a_1 y(t-1)+a_2 y(t-2)+\ldots+a_{n_A} y(t-n_A)+e(t)$ or $A(q^{-1})y(t)=e(t)$ (21)

ARMA model: $y(t)=a_1 y(t-1)+a_2 y(t-2)+\ldots+a_{n_A} y(t-n_A)+e(t)+c_1 e(t-1)+\ldots+c_{n_C} e(t-n_C)$ or $A(q^{-1})y(t)=C(q^{-1})e(t)$ (22)

where y(t) denoted the glucose measurement at current time instant t and y(t−k) is the glucose measurement k time-units before the current time t. $e(t)=y(t)-\hat{y}(t)$ represented the residual terms caused by the difference between the patient's behavior and its model, where $\hat{y}(t)$ was the predicted value of y(t). Parameters $a_i$ and $c_i$ were unknown and were identified by using the patient's GCM data. $q^{-1}$ was the back shift operator that transforms a current observation to a previous one [$q^{-k}(y(t)=y(t-k)$]. Polynomials $A(q^{-1})$ and $C(q^{-1})$ in Equations 21 and 22 were:

$$A(q^{-1})=1-a_1 q^{-1}-\ldots-a_{n_A}q^{-n_A} \quad (23)$$

$$C(q^{-1})=1+c_1 q^{-1}+\ldots+c_{n_C}q^{-n_C} \quad (24)$$

Future glucose concentrations were estimated from recent glucose data, and models did not require any prior information about glycemic disturbances such as meal consumption or insulin administration.

Glucose-insulin dynamics show inter-subject variability. Metabolic changes caused by stress or changes in insulin sensitivity might also lead to variation in glucose-insulin dynamics of the same subject over time. Furthermore, subjects were exposed to glycemic disturbances such as meal consumption or physical activity on a daily basis. A reliable model for predicting glucose levels should address such variabilities and should be able to adapt to unexpected fluctuations in the system dynamics. As a new glucose measurement became available at each sampling instant, model parameters were updated in order to include information about the most recent glucose concentration dynamics. The preferred recursive identification strategy was the weighted recursive least square (RLS) method with a forgetting factor, λ:

$$y(t) = \varphi(t)^T \theta(t) + e(t) \quad (25)$$

$$\hat{\theta}(t) = \hat{\theta}(t-1) + K\{y(t) - \varphi(t)^T \hat{\theta}(t-1)\} \quad (26)$$

$$K(t) = \frac{P(t-1)\varphi(t)}{\lambda + \varphi(t)^T P(t-1)\varphi(t)} \quad (27)$$

$$P(t) = \frac{1}{\lambda}\left[P(t-1) - \frac{P(t-1)\varphi(t)\varphi(t)^T P(t-1)}{\lambda + \varphi(t)^T P(t-1)\varphi(t)}\right] \quad (28)$$

where y(t) was the current glucose measurement, φ(t) represented the vector of past glucose observations, and θ(t) denoted the vector of model parameters, while $\hat{\theta}(t)$ is its estimate. For example, for the ARMA model described by Equation 22, $\varphi(t)=[y(t-1)\ldots y(t-n_A), e(t-1)\ldots e(t-n_C)]$ and $\hat{\theta}(t)=[a_1(t)\ldots a_{n_A}(t), c_1(t)\ldots c_{n_C}(t)]$. K(t) and P(t) were the smoothing parameter and estimate of error variance, respectively. The forgetting factor (0<λ≤1) assigned relative weights on past data sequence. When λ=1, all observations were equally weighted (infinite memory) in the identification.

Small values of λ made the more recent data dominant for estimation of model parameters by assigning larger weights on recent observations and smaller weights on older ones (short memory).

In order to capture unpredicted glycemic disturbances rapidly and to provide quick response to such conditions, the RLS algorithm was integrated with a change detection method. When a persistent change in model parameters was detected, λ was decreased to a smaller value. This way, past observations (data before the change detection) were rapidly excluded, and faster convergence to new model parameters is ensured. However, to avoid parameter changes due to non-persistent abnormalities in data such as sensor noise, λ was not reduced at the first instant of change detection. Instead, consistency of the change for several time steps (window size, $T_W$) was assured first. The change detection method was described by null and alternative hypotheses as:

$$H_0: E(\hat{\theta}(t)) = \theta_0, \text{ for } T < t < T + T_W,$$

$$H_1: E(\hat{\theta}(t)) \neq \theta_0, \text{ for } T < t < T + T_W \quad (29)$$

where $E(\hat{\theta}(t))$ represented the expected value of parameter estimates at current time t and $\theta_0$ is the vector of unbiased parameter estimates computed by the RLS algorithm using data until time instant T. When a persistent change with the duration of the window size is detected, λ was reduced to a smaller value, and $\theta_0$ is replaced with its new estimate.

The k-steps-ahead glucose prediction, $\hat{y}(t+k|t; \theta)$ is a function of current and past glucose observations. For the ARMA model (Eq. 22):

$$\hat{y}(t+k \mid t; \theta) = \frac{G(q^{-1})}{C(q^{-1})} y(t) \quad (30)$$

The polynomial $G(q^{-1})$ (of order $n-1$, $n = \max(n_A, n_C - k + 1, 1)$) was uniquely defined by:

$$C(q^{-1}) = A(q^{-1}) F(q^{-1}) + q^{-k} G(q^{-1}) \quad (31)$$

where $F(q^{-1})$ had order of $k-1$. Rearrangement of Equations 30 and 31 for AR models (Eq. 21) was straightforward.

Prediction accuracy, the deviation of predicted glucose values from the patient's GCM device data, was expressed as the sum of squares of the glucose prediction error (SSGPE):

$$SSGPE \% = \sqrt{\frac{\sum (y - \hat{y})^2}{\sum y^2}} \times 100 \quad (32)$$

and relative absolute deviation (RAD):

$$RAD (\%) = \frac{|y - \hat{y}|}{y} \times 100 \quad (33)$$

In Equations 32 and 33, y denotes the actual glucose measurement (CGM data), and $\hat{y}$ is the predicted glucose concentration. SSGPE and RAD did not depend on data magnitude, since they are normalized by actual glucose measurements. The CGM device was assumed to provide accurate (reference) glucose readings.

Prediction performance was also evaluated using CG-EGA. CG-EGA creates three error grid zones (clinically accurate, benign errors, and erroneous readings) for analyzing the prediction accuracy and provides separate analysis during hypoglycemia (blood glucose≤70 mg/dL), normoglycemia (70<blood glucose≤180 mg/dL), and hyperglycemia (blood glucose>180 mg/dL). The CGM data was used as reference and to analyze the accuracy of the predicted glucose values in terms of CG-EGA.

Glucose prediction with time-invariant models was first demonstrated on the database of study Group A. In order to remove any noise in the sensor data, CGM data was smoothed using a low-pass filter. The first half of the smoothed CGM data was used for the development and identification of the linear models with constant parameters (Eqs. 21 and 22). Then, prediction performances of the models developed were validated on the patient's raw second-day data (second half). Models of various orders ($n_A$, $n_C$) were developed using the MATLAB (Natick, Mass.) System Identification Toolbox. The best model order was determined based on a statistical model fit measure, Akaike's Information Criterion. Results showed an AR model of order 3 ($n_A = 3$) and ARMA model of order (3,1) ($n_A = 3$, $n_C = 1$) to be satisfactory. FIG. 4 demonstrates the predicted glucose values by these models for the representative subjects, with model parameters and prediction error terms provided in Table 2.

TABLE 2

MODEL PARAMETERS AND GLUCOSE PREDICTION ERRORS OF GROUP A

| Patient group, model | Model parameter | | | | SSGPE (%) | Mean RAD (%) |
|---|---|---|---|---|---|---|
| | $a_1$ | $a_2$ | $a_3$ | $c_1$ | | |
| Healthy | | | | | | |
| AR(3) | 1.294 | −0.480 | 0.185 | — | 4.27 | 1.26 (0.27) |
| ARMA(3, 1) | 2.065 | −1.237 | 0.172 | −1.01 | 4.21 | 1.21 (0.28) |
| Glucose-intolerant | | | | | | |
| AR(3) | 1.625 | −1.019 | 0.392 | — | 4.81 | 1.43 (0.35) |
| ARMA(3, 1) | 1.241 | −0.437 | 0.184 | 0.463 | 4.72 | 1.40 (0.32) |
| Diabetes | | | | | | |
| AR(3) | 1.215 | −0.154 | −0.061 | — | 4.20 | 1.11 (0.24) |
| ARMA(3, 1) | 1.844 | −0.886 | 0.042 | −0.669 | 4.11 | 1.09 (0.24) |

Results are for time-invariant models. SSPGE and RAD values are for a PH of two time steps (one step = 5 min). Mean RAD values are reported with standard deviations given in parentheses.

Prediction accuracy defined as SSGPE or RAD (Eqs. 32 and 33) is highly affected by the PH, and how far into the future one is trying to predict. FIG. 5 includes Table 3, which presents mean SSGPE and RAD values for several PH for populations of both study groups. PH=3 denotes that glucose value 3-steps-ahead (15 min) from the current time was predicted using the available history of glucose measurements. For 10-min-ahead prediction, results showed around 4-5% SSGPE and 1-2% RAD. Prediction errors increased to around 11-12% SSPGE and 5-7% RAD for PH=6. Even though prediction models were developed using filtered glucose data, SSGPE and RAD were computed as deviation of predicted glucose values from patient's raw GCM device data.

For constant parameter models, prediction errors were also affected by the likeness between data used for model development and data used for validation. Reducing the interval of data used in model development from 24 hours to 12 hours (from one-half to one-fourth) did not significantly alter the SSGPE and RAD values: e.g., for PH=2 and ARMA(3,1), SSGPE was 5.10±0.97%, 4.25±0.93%, and 5.20±1.06%, and RAD was 1.42±0.15%, 1.21±0.38%, and 1.47±0.37% for the healthy, glucose-intolerant, and type 2 diabetes populations of Group A, respectively. Since glucose concentrations were relatively constant at night and most of the glucose variation occurred during daytime, the model from the first 12-h data was able to capture the dynamics of the remaining data. However, using the first 6-h data for model development significantly increased the error terms for PH=2 and ARMA (3,1) to 8.37±0.96%, 7.28±1.26%, and 8.05±2.21% SSGPE and 3.38±0.37%, 3.31±0.70%, and 3.54±0.72% RAD for healthy, glucose-intolerant, and type 2 diabetes populations, respectively.

For the recursive modeling, ARMA model type was selected over AR since the model error information was leveraged by the ARMA model structure [$C(q^{-1})$ term in Eq. 22]. During recursive identification, simultaneously an online filter was utilized to remove the sensor noise and consequently enhance the prediction accuracy. FIG. 6 illustrates 5-min- (PH=1) and 30-min-ahead (PH=6) glucose predictions for representative subjects of Group B. Results were for ARMA (2,1) with $T_W$=5 (25 min) and λ=0.5. The forgetting factor was reduced to 0.005 in case of change detection. The model was able to track and predict 30-min-ahead glucose concentrations accurately with 3.03% and 6.14% SSGPE and 2.62±0.83% and 3.78±1.12% RAD for the representative healthy and type 2 diabetes subjects, respectively.

Increasing the autoregressive term of ARMA(p,q), p, results in more oscillatory predictions with larger overshoots that cause increase in prediction errors. For instance, the error terms increased to 3.84% and 7.40% SSGPE and 2.85±0.78% and 4.02±1.00% RAD for healthy subjects and patients with diabetes in FIG. 6, for ARMA(3,1) with PH=6. On the other hand, as the model order was reduced to ARMA(1,1), prediction profiles became much smoother; however, they resulted in larger delays in predictions. Reducing the moving average part (q), ARMA(2,0) or AR(2), lead to consistent overshoot and higher SSGPE and RAD values (3.81% and 6.76% SSGPE and 2.80±0.81% and 3.87±1.09% RAD for representative healthy and type 2 diabetes subjects, respectively, in FIG. 6 with PH=6), whereas ARMA(2,2) did not significantly improve the prediction performance.

Prediction capability of the recursive algorithm for model ARMA(2,1) with $T_W$=5 (25 min) and λ=0.5 was evaluated in terms of SSGPE and RAD in Table 4 of FIG. 7. Means and standard deviations of the error terms, up to six time steps of PH are provided for both subject groups. Comparing results of Table 3 with Table 4, for PH=1, the SSGPE and RAD values were slightly lower for time-invariant models because the transition period (start with an untuned model) in the recursive strategy may have lead to large error terms at the beginning and constant-parameter models may have yield smaller error terms for small PH values. As PH increases, the superior predictive capability of the recursive identification was shown by significantly smaller SSGPE and RAD values compared to time-invariant models. Comparison of the results between the study groups in Tables 3 and 4 reveals lower prediction errors for the hospitalized group because glucose variation was reduced under controlled conditions.

Accuracy of the predictions was also evaluated using CG-EGA. In FIG. 8, Table 5 demonstrates the CG-EGA error matrix for 30-min-ahead glucose predictions using the recursive algorithm with change detection. There were no CGM data in the hyperglycemic range for the healthy population; therefore Table 5(A) does not include columns for hyperglycemia. In the hypoglycemic range, 92.31%, 7.69%, and 0% of the data resulted in accurate readings, benign errors, and erroneous readings for the healthy population and 92.94%, 5.29%, and 1.77% for the population with type 2 diabetes. These values were 91.50%, 7.87%, and 0.63% during normoglycemia and 89.79%, 8.70%, and 1.51% during hyperglycemia for the population with type 2 diabetes. In contrast, 95.47%, 4.53%, and 0% of the healthy group data were considered as accurate, benign errors, and erroneous readings during normoglycemia.

To enhance change detection in model parameters, noisy data were smoothed with an online filter. A low-pass equirriple finite impulse response filter was used with normalized pass-band edge frequency of 0.42 and stop-band edge frequency of 0.5. Initial values for model parameters ($\theta(t=0)$) were 0; therefore, initialization did not require any prior glucose concentration data. Model parameters converged to good parameter values rapidly, and reliable glucose concentration predictions were made in less than 2 hours after starting the recursive algorithm (FIG. 9). This period could be reduced further for a specific patient who uses this method routinely, by assuming as the initial value the parameter values from an earlier prediction series.

Adaptive System for Estimating Future Glucose Concentrations

This example considered a time-series model that captured dynamical changes in the glucose metabolism. Univariate models developed from a subject's continuous glucose measurements were compared to multivariate models that were enhanced with continuous metabolic, physical activity, and lifestyle information from a multi-sensor body monitor. A real life application for the proposed algorithm was demonstrated on early (30 min in advance) hypoglycemia detection.

Data used in this study consisted of glucose concentration data and physiological signals collected over a period of 20 days from a subject with type 2 diabetes under free living conditions. The subject had no constraints on food or exercise over the data collection period. He consumed the food that he usually ate and exercised daily according to his usual routine (he rode his bicycle to work and frequently rode longer distances for exercise). A Medtronic MiniMed Continuous Glucose Monitor, MMT-7012 (Medtronic MiniMed, Northridge, Calif.) was used to gather the glucose data. This device measured subcutaneous glucose concentrations every five minutes. The body monitoring system SENSEWEAR Pro3 (BodyMedia Inc., Pittsburgh, Pa.) was used for collection of metabolic, physical activity and lifestyle information. The armband weighed 80 g and was worn on the upper right arm without obstructing daily activities. The device consisted of four sensors: (1) a heat-flux sensor that determined the rate at which heat is dissipating from the body by the measurement of heat loss between the skin and a vent on the side of armband, (2) a temperature sensor that measured the surface temperature of the skin, (3) a galvanic skin response sensor that measured skin impedance which varies due to sweating and emotional stimuli reflected by water content of the skin and the constriction or dilation of the vascular periphery, and (4) a two-axis accelerometer which tracked movement and body position and measures motion activity. The armband provided a total of seven signals to describe the subject's activity and emotional conditions: energy expenditure, average longitudinal acceleration, transverse acceleration peaks, transverse acceleration mean of absolute difference, near-body temperature, heat flux and galvanic skin response. The SENSEWEAR monitor provided measurements every minute, therefore the physiological data was trimmed to include the data points at the same time instants as those from the glucose monitor. The subject was allowed to live normally, as no requirements were set as to food consumption or exercise.

After identification of the model parameters at each step using the weighted RLS and the change detection method, the following univariate model (now with known parameters)

$$y_k = \phi_{k-1}^T \hat{\theta}_{k-1} + e_k = \hat{y}_k + e_k$$

was easily appended m-steps into the future to predict the future excursion of glucose concentrations ($\hat{y}_{k+m|k; \hat{\theta}_k}$) which was a linear function of current (yk) and past (yk−i) glucose measurements. Appending the multivariate model of m-steps into the future required future values of the exogenous inputs (u(i)k+j) which were unknown until new measurement became available. For this situation, the input variables, Uk=[u(1)k ... u(n)k]T, were assumed to follow a vector ARMA model of orders nA and nC:

$$U_k = \sum_{i=1}^{n_A} A_{i,k} U_{k-i} + \sum_{i=1}^{n_C} C_{i,k} \varepsilon_{k-i} + \varepsilon_k$$

where Uk=[u(1)k ... u(n)k]T and εk=[ε(1)k ... ε(n)k]T were considered the system output and the noise vectors of length n, respectively. Ai,k and Ci,k were the m×m matrices composed of model parameters at sampling step k:

$$A_{i,k} = \begin{bmatrix} a_{11,i} & \cdots & a_{1m,i} \\ \vdots & \ddots & \vdots \\ a_{m1,i} & \cdots & a_{mm,i} \end{bmatrix}_k \quad C_{i,k} = \begin{bmatrix} c_{11,i} & \cdots & c_{1m,i} \\ \vdots & \ddots & \vdots \\ c_{m1,i} & \cdots & c_{mm,i} \end{bmatrix}_k$$

Using the 20-day data from the CGMS and SENSEWEAR armband, various ARMA and multivariate ARMAX models of different structures (different variable combinations) and different orders (nA, nC, nB) were developed. Model order selection was performed for constant parameters case where models were compared based on a statistical model fit measure, Akaike information criterion (AIC), over the entire data to find the best fitting model. AIC rewards the goodness-of-fit, but with a trade-off for over-parameterization.

MATLAB System Identification Toolbox (The MathWorks Inc., Natick, Mass.) was used for preliminary model order selection. For the univariate ARMA model of (1), results show nA=2 and nC=1 to describe the best model (lowest AIC value). For the multivariate ARMAX model, it was found that among the 7 signals from the armband, only 5 had significant contribution to the glucose metabolism or excursions. Those five signals were identified as: energy expenditure (EE), average longitudinal acceleration (LA), heat flux (HF), galvanic skin response (GSR), and near-body temperature (BT). The contributions of the remaining two signals (transverse acceleration peaks and transverse acceleration mean of absolute difference) were shown to be included in the energy expenditure signal. The model orders for the multivariate model were nA=2, nB=[1, 1, 2, 2, 2] and d=[4, 4, 5, 7, 5] for the input vector U=[EE, LA, HF, GSR, BT], and nC=1.

Next, the proposed recursive identification algorithm was implemented for models with determined orders. The total numbers of model parameters needed to be identified were 3 and 11 for the univariate and multivariate models, respectively. At each sampling step, the model parameters were identified using. Then with known parameter values, the univariate and multivariate models were appended for m-steps to compute the m-step-ahead predicted glucose concentration. Initial values for the parameter vector was assigned zero.

Figure 10:
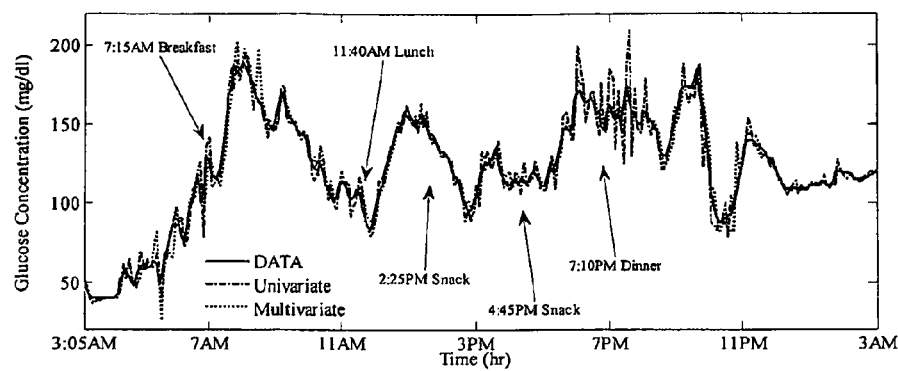
FIG. 10 is a graph summarizing glucose prediction with multivariate and univariate models for a typical 24 hour period, according to one of the examples.

FIG. 10 illustrates a 24 hour portion of the data which represents a typical day for the patient. The proposed algorithm was implemented at the start of that day (3:05 AM) with NW=5 steps, λ=0.5 and the initial parameter vector as 0 (untuned model), meaning that no prior data was used for tuning the model. FIG. 10 demonstrates prediction of glucose values for both multivariate and univariate models 30 min ahead. As expected, it took longer for the multivariate model to tune to true patient dynamics (oscillations in the first hours), since it required identification and convergence of a larger number of model parameters (11 versus 3). However, after the initial tuning period, predictions with the multivariate model followed the CGMS measurements more closely than the univariate model, which demonstrated larger undershoots or overshoots. This confirmed the hypothesis that physiological signals supplement the CGM information and enhanced the prediction accuracy of the glucose predicting models (also see Table 6).

Figure 11:
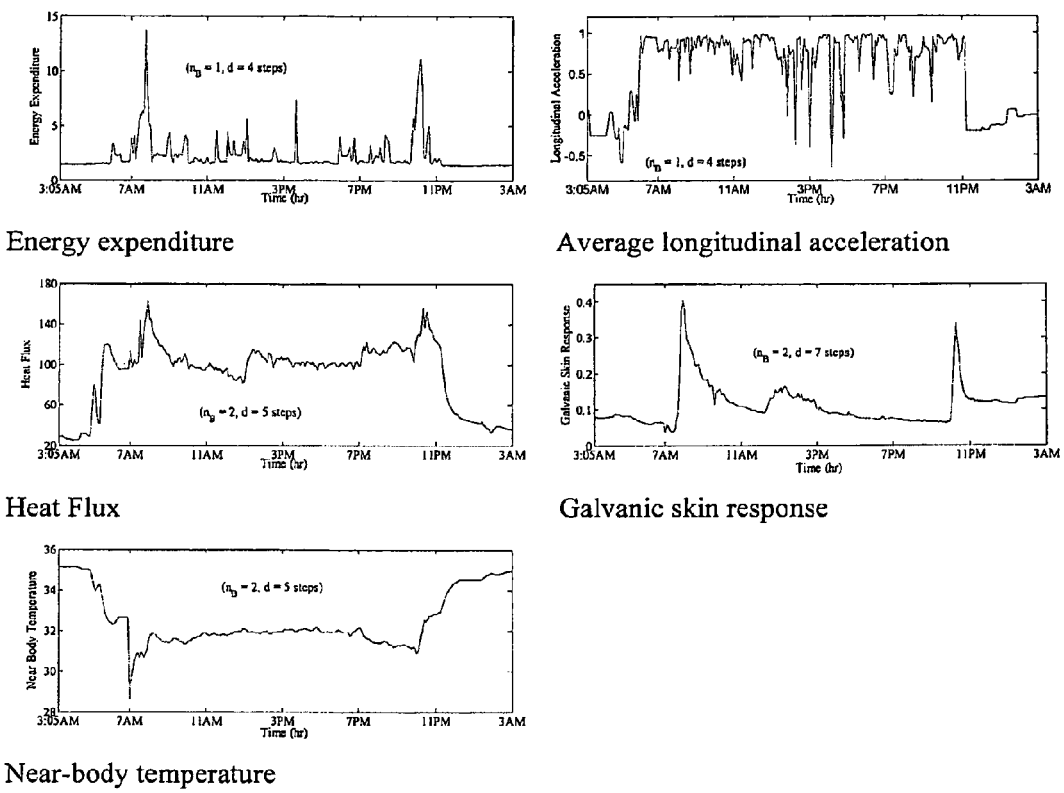
FIG. 11 includes graphs of physiological signals from the physiological sensor used for the multivariate model in FIG. 10.

FIG. 11 demonstrates the SENSEWEAR armband signals used for the development of the multivariate model in FIG. 10. The number of parameters used to describe each individual signal in the model is given by nB, and the delay term d describes the time-steps elapsed until the effect of a specific signal becomes detectable on glucose excursion.

Prediction performance was numerically evaluated using the two error metrics that describe the deviation of the m-step-ahead predicted values ($\hat{y}_{k|k-m; \hat{\theta}_{k-m}}$) from the actual observed CGMS data (yk): the relative absolute deviation (RAD) and the sum of squares of the glucose prediction error (SSGPE).

$$RAD\ (\%) = \frac{|y_k - \hat{y}_{k|k-m; \hat{\theta}_{k-m}}|}{y_k} \times 100$$

$$SSGPE\ (\%) = \sqrt{\frac{\sum (y_k - \hat{y}_{k|k-m; \hat{\theta}_{k-m}})^2}{\sum y_k^2}} \times 100$$

The summation terms for SSGPE were over total number of observations in the data. The SSGPE gives more penalty to larger deviations (squared deviation) compared to smaller ones. Both metrics did not depend on data magnitude (number of observations), since they are normalized by actual glucose measurements.

Table 6 presents the prediction performance of the proposed algorithm over the entire study period. The means of error metrics (RAD and SSGPE) were reported for both multivariate and univariate models. Results were for 30 min ahead prediction (m=6 steps) with NW=5 steps (25 min) and λ=0.5. The forgetting factor was reduced to 0.005 in case of change detection. Results in Table 6 demonstrate that prediction accuracy was improved and errors metrics were decreased with the multivariate model compared to the univariate model.

TABLE 6

Prediction performance for the 20 day data: Reported are mean values with standard deviations given in parentheses.

|  | Univariate Model | Multivariate Model |
|---|---|---|
| RAD (%) | 5.51 (6.11) | 4.56 (6.15) |
| SSGPE (%) | 7.33 | 5.74 |

Application as Early Hypoglycemia Detection

The proposed multivariate glucose prediction algorithm can be used to predict future hypoglycemic episodes before they occur, allowing time for necessary corrective action. When the m-step-ahead predicted glucose level ($\hat{y}_{k+m|k}; \hat{\theta}_k$) is below an assigned threshold (e.g., 60 mg/dl) value for hypoglycemia, an alarm can be triggered at that sampling instant, k. The alarm signifies that the patient will experience a hypoglycemia m-steps-ahead from the current time.

The prediction of hypoglycemia (alarm issued) was considered false positive if the reference blood glucose measurement at time step k+m is above the defined threshold, and true positive if it was below the threshold value. False negatives occur when the alarm was not issued at the kth step (hypoglycemia not predicted), but the reference glucose at step k+m was actually below the threshold value.

Out of a total of 5903 sampling steps for the 20 day data, the patient experienced hypoglycemia (measured glucose below and equal to 60 mg/dl) during 66 steps (for 330 min). Of these 5903 decisions, 5819 were true negative (alarm not-issued correctly), 51 true positive (alarm issued correctly), 15 false negative (missed alarm), and 18 false positive (alarm issued incorrectly). Sensitivity to detect early hypoglycemia which was defined as the probability of true positive alarms among all the hypoglycemic events occurred was 77% with a false alarm rate of 26% (probability of false alarms among all hypoglycemic alarms triggered; false alarm rate=false positive/[false positive+true positive]).

Figure 12:
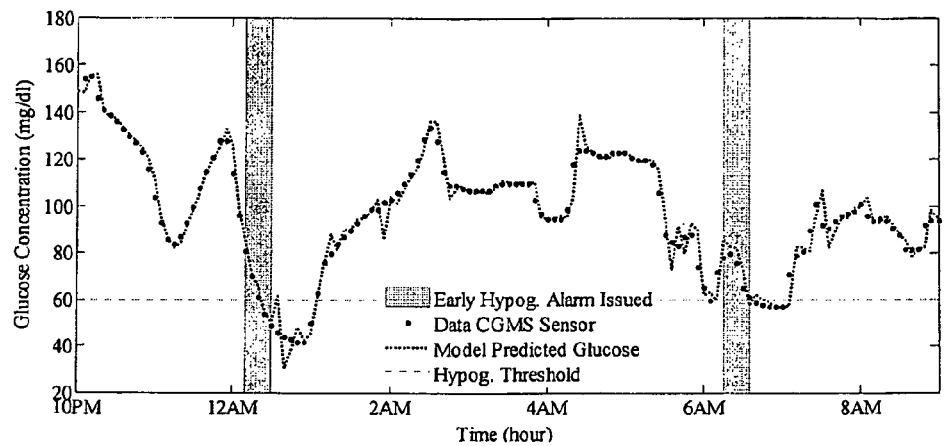
FIG. 12 demonstrates early hypoglycemic alarms with the proposed multivariate algorithm for 30-min-ahead prediction.

FIG. 12 illustrates a portion of the 20 day data when the patient experiences hypoglycemia. Shown are the actual CGMS sensors measurements and 30-min-ahead predicted glucose values (with the multivariate model) for the time region. The shaded areas in the figure represent the period of early alarms that predicted an incidence of hypoglycemia within the next 30 min. The patient experienced two nocturnal hypoglycemic episodes, each correctly alarmed 30 min before their occurrences. Each alarm triggered lasted for 20 min.

Figure 13:
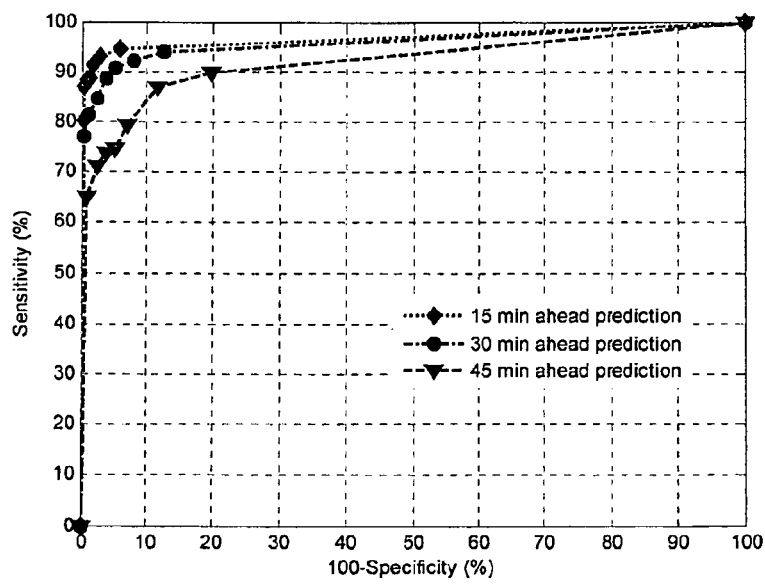
FIG. 13 includes ROC curves for prediction horizons of 15, 30 and 45 minutes ahead.

Selected threshold value for hypoglycemia has a significant effect on alarm performance. Increasing the threshold will improve the sensitivity of the alarms to detect hypoglycemia, but at a cost of decreased specificity (a measure used to correctly identify the absence of hypoglycemic events). Another parameter that affects the alarm performance is the prediction horizon (PH). The sensitivity can further be improved by reducing the PH. However, PH should extend long enough to ensure the time for the necessary intervention (e.g. food ingestion) to avoid hypoglycemia. FIG. 13 illustrates the receiver operating characteristic (ROC) curves for 15-, 30-, and 45-min-ahead predictions. The markers on each ROC curve correspond to a different threshold (at 10 mg/dl intervals); with the lowest sensitivity at 60 mg/dl and the highest at 120 mg/dl.

The modeling algorithm estimated future glucose levels using the subject's glucose and physiological measurements, and did not require any prior experimental data, tuning for each subject, or disturbance information. Therefore, the model of this invention can be implemented for any subject using a CGM sensor a multi-sensor body monitor. The prediction performance analysis demonstrated that the error metrics of RAD and SSGPE were significantly reduced with additional measurements from the armband (multivariate model), when compared to predictions done solely on glucose measurements (univariate model). Results showed 5.51±6.11% RAD and 7.33% SSGPE with the univariate model, when predicting 30 min into the future. The error metrics reduced to 4.56±6.15% RAD and 5.74% SSGPE with the multivariate model which proves the significant effect of physiological signal on glucose metabolism.

The proposed multivariate algorithm provided 30-min-ahead predicted glucose values that closely follow the sensor data (FIG. 11), which improved the alarm performance (sensitivity). Results showed that sensitivity to detect hypoglycemia was 77% with false alarm rate of 26% for prediction horizon of 30 min and 60 mg/dl hypoglycemia threshold. The ROC curve analyses have shown that sensitivity can further be improved by either reducing the PH or increasing the alarm threshold. However, improved sensitivity comes with a cost of increased number of false alarms, which might frustrate patients and make them ignore the alarms.

Adaptive Closed Loop Strategy for Regulation of Blood Glucose Levels

In this Example, the performance of the adaptive closed-loop strategy of this invention was investigated using two virtual patient simulators for type 1 diabetes; one utilizing models of GlucoSim (GlucoSim: A web-based educational simulation package for glucose-insulin levels in human body, [Online]. Available: http://216.47.139.196/glucosim/) and the other utilizing models developed by Hovorka et al. (R. Hovorka et al., Nonlinear model predictive control of glucose concentration in subjects with type 1 diabetes, Physiol. Meas. 25 (2004) 905-920; R. Hovorka et al., Partitioning glucose distribution/transport, disposal, and endogenous production during IVGTT, AJP-Endo. 282 (2002) E992-E1007). Sensor noise with a standard deviation of 2.5 mg/dl was added to the data from both GlucoSim and Hovorka models. The peripheral glucose concentration from GlucoSim was assumed to depict a subcutaneous CGM sensor data, while the plasma glucose concentration of Hovorka was delayed for 5 min to depict such a sensor signal. The feasibility of the algorithm was examined for the most delayed route (subcutaneous glucose measurement-subcutaneous insulin delivery), and therefore the most-difficult case for the blood glucose control problem. In this example, tight glucose control was defined with postprandial glucose levels below 160 mg/dl and normalization of glucose levels back to fasting range (120-70 mg/dl) within 2-3.5 h after a meal challenge.

The following autoregressive integrated moving-average model with exogenous inputs (ARIMAX):

$$A(q^{-1})y_k = q^{-d}B(q^{-1})u_{k-1} + \frac{C(q^{-1})}{\Delta}e_k,$$

with constant model order was assumed ($n_A$, $n_B$ and $n_C$ constant), therefore only the model parameters were identified at each sampling step. The model order was selected based on physiological insight about the action of subcutaneously administered rapid-acting insulin. Action curves of subcutaneously administered rapid-acting insulin were known to show onset within 5-15 min, peak in 45-90 min and overall duration about 3-4 hours. Assuming that insulin will have its most dominant effect on glucose regulation until its peak time, $n_B=12$ (control action with duration of 60 min) and delay of 3 steps (onset of 15 min) was selected. $n_A=2$, $n_C=1$ was assumed and initial model parameters were taken as zero except $b_0=1$. More precise selection of model order and initial parameters can be performed using system identification techniques; however in real-life this can require an additional step of prior studies or experiments. In this example, such steps were skipped and the time period (or transition period) required for system to tune itself and the cost of such periods was investigated. Forgetting factor $\lambda=0.5$ was used and its value was reduced to 0.005 in case of change detection for one sampling instant. The lower limit of $\lambda$ was selected close to 0 in order to facilitate the convergence to new model parameter values and to avoid tuning steps which might be required with selection of larger limit values.

Other design parameters for the proposed control structure included the weight on input and output terms in the quadratic cost functions, and the prediction horizons for control input ($N_u$) and output ($N_y$) in a generalized predictive control (GPC) model, as discussed in Eren-Oruklu et al., Adaptive Control Strategy for Regulation of Blood Glucose Levels in Patients with Type 1 Diabetes, Journal of Process Control 19 (2009) 1333-1346, herein incorporated by reference. Prediction horizons (PH) were $N_y=20$ and $N_u=15$. Several q/r ratios were investigated and a ratio of 5 was selected. In addition to the exponential reference trajectory, the effort on trajectory tracking was increased by increasing the q/r ratio by 3-fold for glucose concentrations below 80 mg/dl to provide faster recovery from hypoglycemia.

A constant time-delay:

$$\frac{dG_{subc,meas}}{dy} = \frac{1}{\tau}G_{blood} - \frac{1}{\tau}G_{subc,meas}.$$

was assumed between subcutaneous and blood glucose concentrations. Comparing blood and peripheral glucose excursions of GlucoSim, a time-constant around 4-5 min was identified for our system which was consistent with the values reported in literature. Similarly, the blood glucose values of the Hovorka model were delayed by 5 min to represent subcutaneous measurements. $\tau$ values of 7.1±5.5 min and 2.2±6.2 min have been reported for two commercial subcutaneous CGM sensors. More recently, $\tau$ values of 4-10 min and values less than 5 min have been reported.

Figure 14:
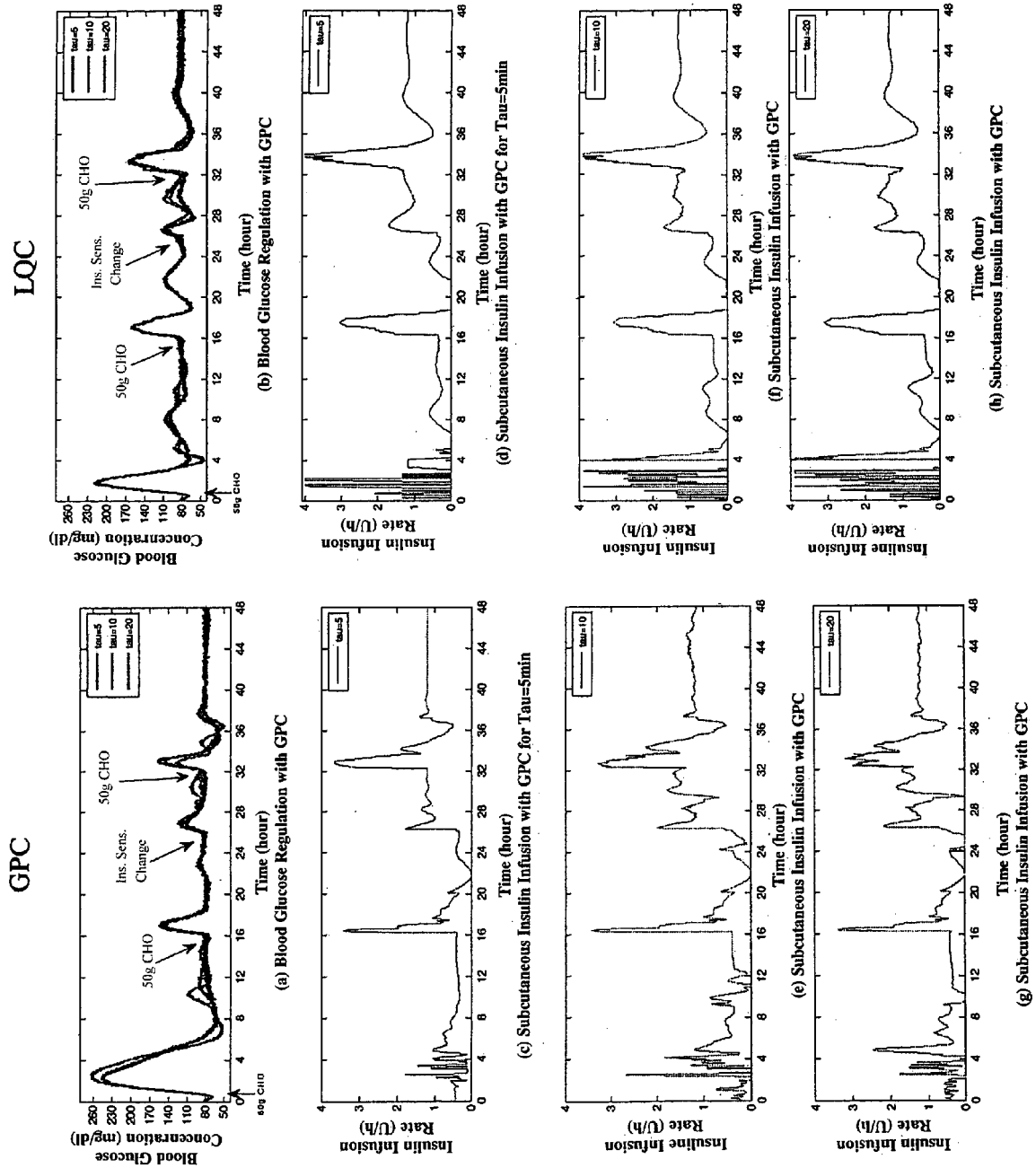
FIG. 14 shows glucose regulation in response to three meal disturbances (50 g CHO at 30 min, 16 h and 32 h after closing the loop) with simultaneous challenge in insulin sensitivity (70% reduction in insulin sensitivity at 26 h) for virtual patients simulated with GlusoSim, with subcutaneous insulin delivery using the GPC (left) and LQC (right) strategies.

FIG. 14 shows glucose regulation with the proposed GPC and a linear quadratic control (LQC) strategy, as described in detail in Eren-Oruklu et al., Journal of Process Control 19, in response to three-meal challenges (each of 50 g CHO content, consumed 30 min, 16 h and 32 h after closing the loop) with simultaneous change in patient's insulin sensitivity at 26 hours using the GlucoSim model. Changes in insulin sensitivity were generated with variation of rate constants of insulin-dependent glucose uptake and liver glucose production in GlucoSim models. Similarly, the three insulin sensitivity indexes were varied from their reported nominal values to simulate a patient with changing insulin resistance. For both simulators, insulin sensitivity parameters are varied with 10% increments, in the range of −70% to +30% of their nominal values. An asymmetric range was selected, so that the population represented more of an 'unstable' (insulin resistant) patient group.

Figure 15:
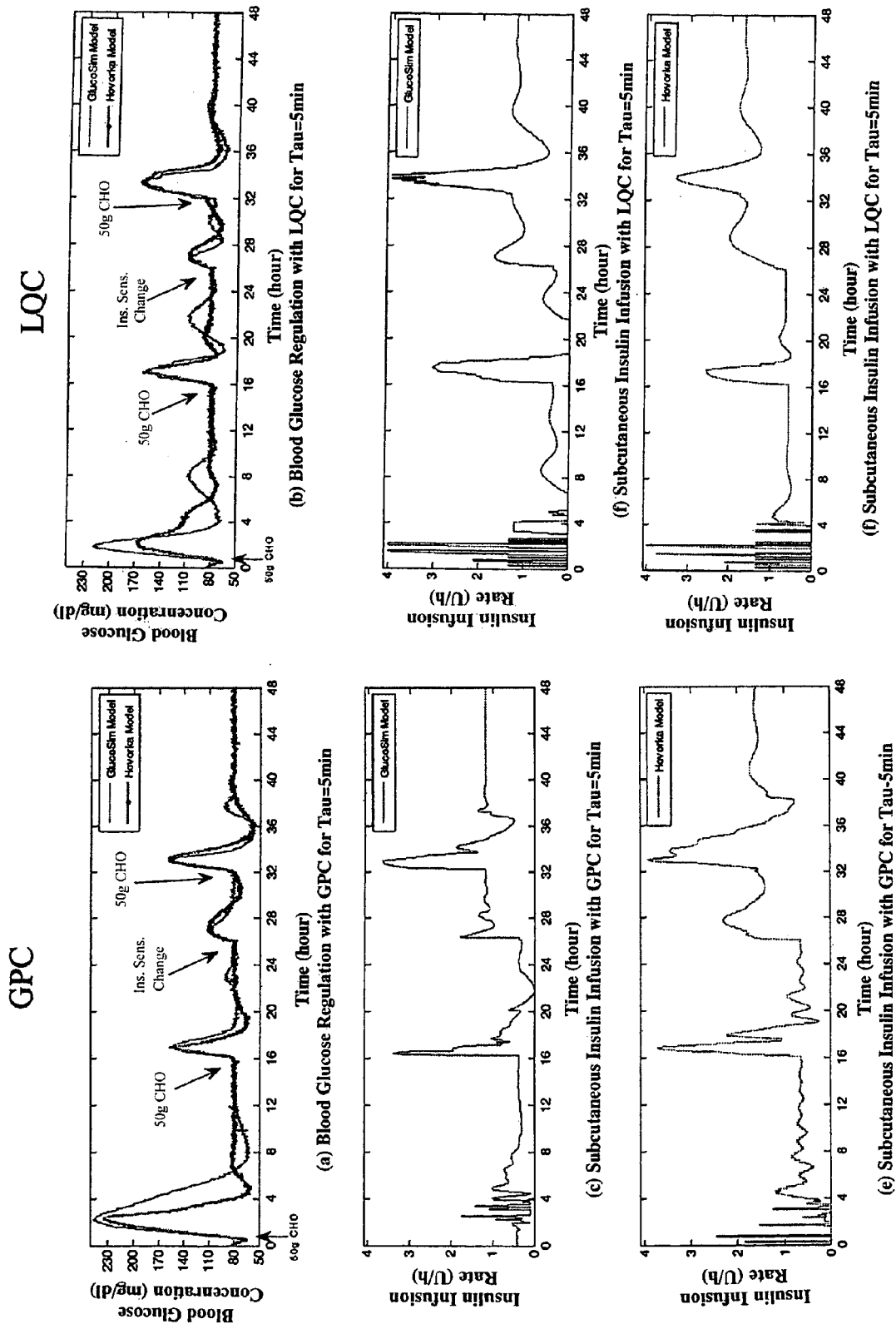
FIG. 15 shows glucose regulation in response to three meal disturbances (50 g CHO at 30 min, 16 h and 32 h after closing the loop) with simultaneous challenge in insulin sensitivity (70% reduction in insulin sensitivity at 26 h) for two virtual patients simulated with GlusoSim and Hovorka models.

In FIG. 14, a subject was assumed to have regular insulin sensitivity at the beginning (nominal value) and experience significant reduction in insulin sensitivity of 70% (the worst case) at 26 hours. Results were for r=5 min, and overestimated $\tau$ values (10 min and 20 min) were also included. FIG. 15 presents glucose regulation using the proposed GPC and LQC strategy on a patient simulated by the Hovorka model. Results were for $\tau$=5 min, the same case scenario with same design parameters. For comparison, results of FIG. 14 for r=5 min are also included in FIG. 15.

The transition period which was defined as time elapsed until the system tunes itself was clearly detected in insulin infusion rate plots in FIGS. 14 and 15. GlucoSim and the Hovorka models show similar behavior during this time period, and the transition period is around 4 hours for both GPC and LQC. Control action was aggressive and rapidly changing at the start (since the example started with an untuned model or far away from true glucose dynamics) and gradually smoothed as more data became available to capture true glucose dynamics. GPC demonstrated less aggressive control action during this period compared to LQC. Neither control strategy caused severe hypoglycemia (glucose concentration below 50 mg/dl, for $\tau$=5 min) during the transition period since constraint on $\Delta u_k$ avoided excessive insulin administrations.

The effective response of the algorithm according to this invention to external glycemic disturbances was observed with the rapid insulin action taken at meal times (16 h and 32 h, excluding the meal consumed during the transition period) in FIGS. 14 and 15. The algorithm was able to detect and provide a fast response to physiological variations (rapid insulin action at 26 h when insulin sensitivity is reduced, and much higher insulin infusion rates are required during fasting conditions). The closed-loop strategy was able to keep blood glucose regulation within the desired limits even for the most insulin insensitive subject. For $\tau$=5, GPC achieved postprandial glucose peaks at 154.2 mg/dl and 156.2 mg/dl after the meals at 16 h and 32 h respectively for the GlucoSim model, and 155.2 mg/dl and 158.7 mg/dl for the Hovorka model, while postprandial maximums of LQC are 157.2 mg/dl and 164.6 mg/dl for GlucoSim and 157 mg/dl and 167.4 mg/di for the Hovorka model. With the significant reduction in insulin sensitivity, the LQC and GPC strategies lead to postprandial slight hyperglycemia and slight hypoglycemia, respectively. However, neither strategy lead to hyper or hypoglycemic-episodes (blood glucose above 180 mg/dl or below 50 mg/dl) for either model after the initial model identification period. Even in case of insulin insensitivity reduction, both algorithms were able to settle to desired basal glucose levels (80 mg/dl). The glucose peak following the first meal would be much lower if the simulation were started with initial model parameter values tuned for the subject in priori. The lower values of the peaks on the other meals illustrated this case.

Various statistics that defined the mean population performance of blood glucose control are presented in Table 7. Since glucose regulation during the initial model identification and tuning period would not provide true performance statistics for closed-loop strategies, control performance was evaluated for the 16-48 hour time period when the controller was tuned. Special consideration was taken in the selection of the starting time of the performance evaluation window (16 h)

to assure that both controllers reached steady state (basal) conditions after the transient period of the first meal.

TABLE 7

Closed-loop Performance for 2-Equal Size Meals with Simultaneous Insulin Sensitivity Challenge.

| | GlucoSim Model | | | | | | Hovorka Model | |
|---|---|---|---|---|---|---|---|---|
| | GPC | | | LQC | | | GPC | LQC |
| | $\tau = 5$ | $\tau = 10$ | $\tau = 20$ | $\tau = 5$ | $\tau = 10$ | $\tau = 20$ | $\tau = 5$ | $\tau = 5$ |
| $G_{mean}$ (mg/dl) | 89.20 | 90.59 | 89.52 | 91.74 | 94.04 | 95.19 | 87.68 | 92.11 |
| | (4.39) | (5.20) | (5.78) | (4.30) | (5.29) | (6.29) | (3.12) | (4.29) |
| $G_{max}$ (mg/dl) | 152.69 | 158.73 | 156.49 | 159.08 | 159.13 | 160.84 | 155.94 | 161.44 |
| | (6.21) | (5.93) | (5.64) | (6.71) | (6.49) | (4.70) | (6.03) | (4.34) |
| $G_{min}$ (mg/dl) | 64.22 | 63.56 | 61.49 | 67.58 | 69.90 | 64.02 | 63.24 | 70.24 |
| | (5.77) | (5.24) | (4.64) | (5.53) | (5.98) | (4.82) | (7.33) | (4.07) |
| $G_{settle}$ (mg/dl) | 80.57 | 80.94 | 78.89 | 80.83 | 84.47 | 85.94 | 80.31 | 80.64 |
| | (1.04) | (1.24) | (3.18) | (1.35) | (4.33) | (3.67) | (0.95) | (1.19) |
| $t_{100BG}$ (min) | 116.05 | 118.24 | 112.75 | 139 | 142.67 | 144.65 | 117.50 | 141.5 |
| | (8.27) | (8.93) | (15.18) | (6.73) | (7.14) | (7.08) | (10.9) | (14.2) |
| $AUC_{ins} \times 10^2$ (mU) | 354.83 | 367.33 | 373.65 | 339.79 | 356.55 | 347.08 | 489.19 | 478.23 |
| | (58.5) | (53.83) | (55.30) | (63.52) | (59.20) | (60.12) | (50.60) | (53.27) |
| NSSD (%) | 2.37 | 2.50 | 3.18 | 2.42 | 2.58 | 2.84 | 2.26 | 2.30 |
| | (0.62) | (0.46) | (0.72) | (0.85) | (0.67) | (0.85) | (0.34) | (0.30) |
| Subjects$_{60-50, BG}$ | 21 | 24 | 50 | 0 | 0 | 11 | 23 | 0 |
| Subjects$_{BG<50}$ | 0 | 0 | 0 | 0 | 0 | 0 | 0 | 0 |
| Subjects$_{160-180, BG}$ | 3 | 0 | 0 | 56 | 50 | 51 | 7 | 26 |
| Subjects$_{BG>180}$ | 0 | 0 | 0 | 0 | 0 | 0 | 0 | 0 |

The patient population was created by varying the insulin sensitivity indexes of the models by 10% increments in the range of −70% to +30% of their nominal values (total of 11 possible moves). By allowing repetition of the insulin sensitivity value during the second day to include the no-change case, a population with total of 121 patients each experiencing a different insulin sensitivity change scenario was simulated for both models. Table 7 reports population mean results for the GlucoSim model and the Hovorka model (for τ=5 min only), respectively. Compared to GPC, LQC resulted in more sluggish control action with smaller values for the area under the curve ($AUC_{ins}$) of insulin, and consequently higher mean and maximum glucose concentration levels for both models. Neither control strategy causes hypoglycemic or hyperglycemic episodes (number of Subject$_{BG<50}$ and Subjects$_{BG>180}$ is 0). For Glucosim and Hovorka models, 21 and 23 out of 121 cases resulted in slight hypoglycemia (Subjects$_{60-50,BG}$ with τ=5 min) that were recovered within 10 min with GPC, and both models lead to 0 cases with LQC. The feasibility of the proposed closed-loop strategy is further demonstrated as both algorithms are able to bring blood glucose levels back below to 100 mg/dl within 2-2.5 h ($t_{100BG}$).

Deviations from the desired reference trajectory (NSSD) were also reported in Table 7. The normalized sum of squared deviations (NSSD) was computed using:

$$NSSPE\% = \sqrt{\frac{\sum(y-\hat{y})^2}{\sum y^2}} \times 100,$$

where y represented the current desired glucose value (which depends on previous-step glucose measurement), and ŷ represented the actual achieved glucose concentration at the current sampling step. By definition, this equation also penalizes the difference between desired and actual glucose even when the achieved glucose level is better than the desired. Therefore, a conditional strategy was applied: for glucose levels below 80 mg/dl, deviations was included only if ($y_k - \hat{y}_k$)≥0, and for glucose levels above 80 mg/dl, only ($y_k - \hat{y}_k$)≤0 are included. For both models, glucose regulation with LQC lead to higher deviation terms (NSSD) compared to GPC (Table 7) as expected from the more sluggish control actions in FIGS. 14 and 15.

Table 7 also provides the performance statistics for overestimated τ values (10 and 20 min). For some systems the true lag (τ value) between the subcutaneous and blood glucose levels may not be attainable, and one may only have a rough estimation of its value. The statistics in Table 7, and glucose concentration plots of FIG. 14 reveal that for τ overestimations closer to true system dynamics (10 min for our case) the algorithm is still able to provide good glucose regulation. However, glucose regulation starts to deteriorate as the τ estimate diverges from its true value (20 min).

Figure 16:
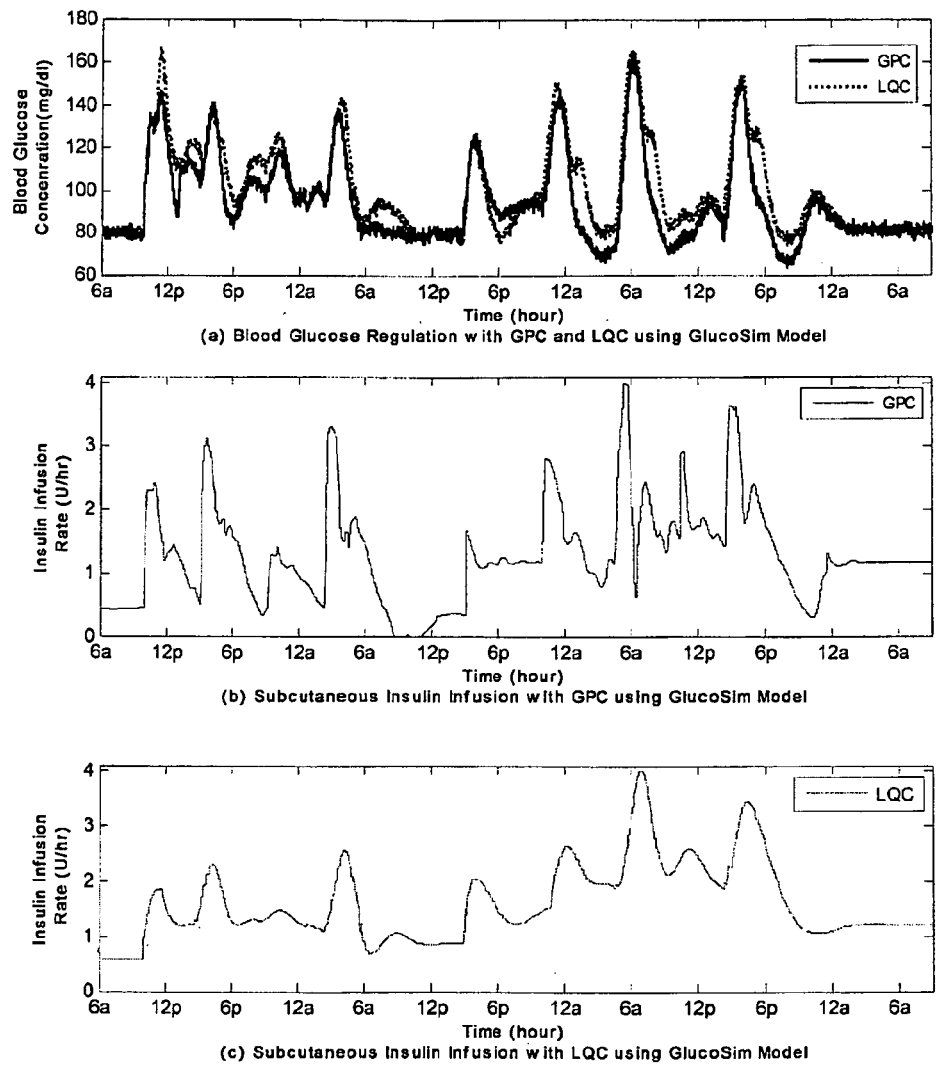
FIG. 16 shows a comparison of glucose regulation with subcutaneous insulin delivery for GPC versus LQC. Closed-loop response in presence of simultaneous multiple meal and insulin sensitivity challenge (70% reduction at 4 AM during the $2^{nd}$ day). Results are for $\tau=5$ and a virtual subject simulated with the GlucoSim model.
Figure 17:
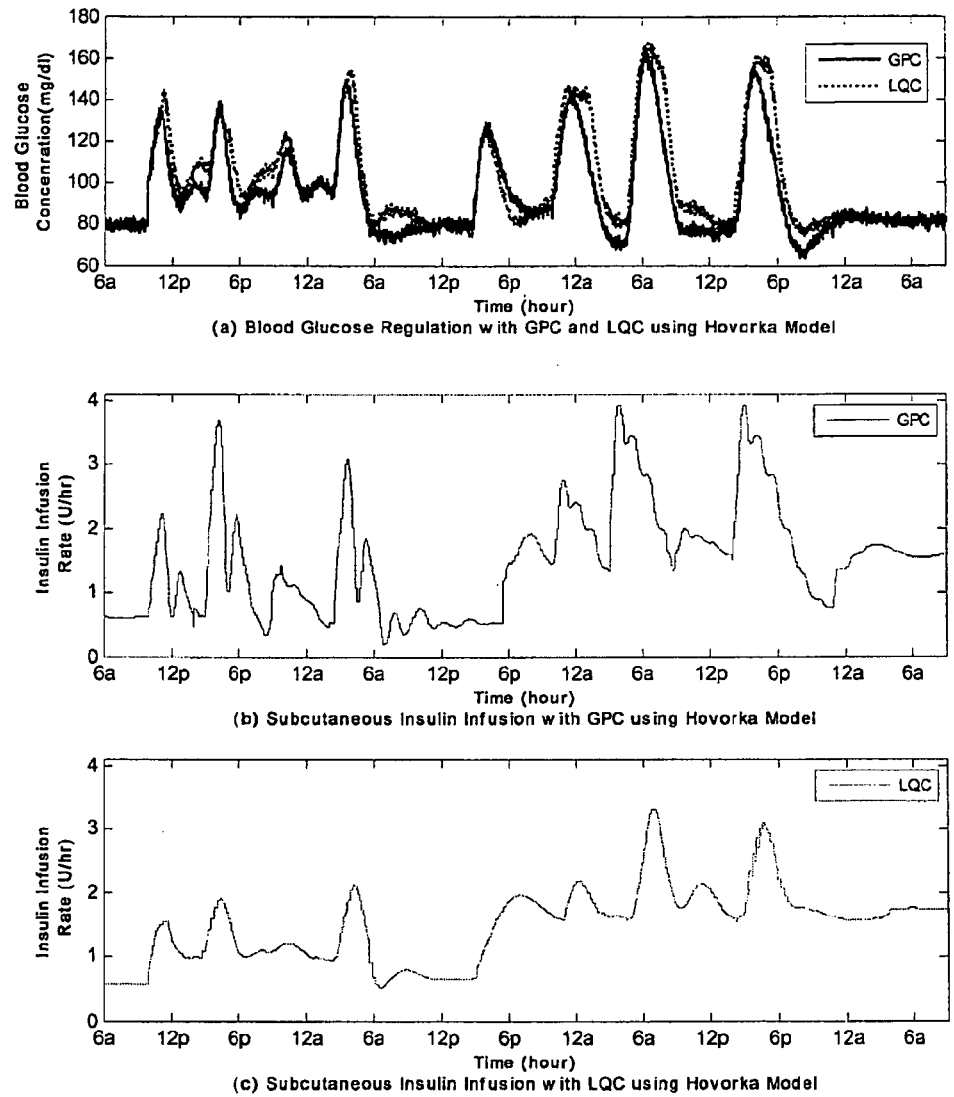
FIG. 17 shows a comparison of glucose regulation with subcutaneous insulin delivery for GPC versus LQC. Closed-loop response in presence of simultaneous multiple meal and insulin sensitivity challenge (70% reduction at 4 AM during the $2^{nd}$ day). Results are for $\tau=5$ and a virtual subject simulated with the Hovorka model.

The performance of the closed-loop algorithm according to this invention was also tested for a more realistic scenario of 2-day multiple meal challenges with changes in the diet and simultaneous changes in insulin sensitivity on the second day. The meal and change in the diet scenario were the same as the discussed above, and the insulin sensitivity scenario is the same as in FIGS. 14 and 15 (70% reduction in insulin sensitivity) with change occurring at 4 AM of the second day. FIGS. 16 and 17 provide blood glucose regulation results with both GPC and LQC for the 2-day multiple meal disturbance challenge for τ=5 using the GlucoSim and Hovorka models respectively. Initial transition periods for identification and tuning were not included in the plots for a clearer representation of the plots and because they display the same characteristics as in FIGS. 14 and 15 (transition period of 4 h). Postprandial glucose maximums slightly over 160 mg/dl were observed for both LQC (Glucosim 166.18 mg/dl, Hovorka 167.16 mg/dl) and GPC (GlucoSim 162.84 mg/dl, Hovorka 164.01 mg/dl) during the second day when lunch challenge was increased by 50% and the patient also experienced the worst insulin sensitivity case. GPC demonstrated faster adaptability (rapid insulin rise coinciding with meal timings) and therefore more active control actions which resulted in lower postprandial peaks and faster normalization of blood glucose concentrations after meals.

Table 8 provides the population mean performance statistics for the 2-day multiple meal challenge. LQC resulted in more sluggish control action compared to GPC with smaller $AUC_{ins}$ higher mean and maximum glucose concentrations, and higher deviation terms for both models. LQC does not lead to any hypoglycemic or hyperglycemic episodes or slight hypoglycemia ($Subject_{BG<50}$=$Subject_{60-50,BG}$=$Subject_{BG>180}$=0). None of the cases resulted in hypoglycemic or hyperglycemic episodes for GPC, while 13 and 14 out of 121 cases showed slight hypoglycemia for GlucoSim and Hovorka models, respectively. Both control algorithms provided satisfactory glucose control performance by bringing back the postprandial glucose levels to normoglycemic limits within the desired 2-3.5 h and avoiding any hypoglycemic episodes or severe hyperglycemia (glucose levels below 50 mg/dl or above 180 mg/dl).

TABLE 8

Closed-loop Performance for 2-Day Multiple Meal (Change in Diet) with Simultaneous Insulin Sensitivity Challenge.

| | GPC | | LQC | |
|---|---|---|---|---|
| | GlucoSim Model | Hovorka Model | GlucoSim Model | Hovorka Model |
| $G_{mean}$ (mg/dl) | 95.75 | 96.72 | 103.26 | 102.50 |
| | (6.94) | (6.82) | (5.64) | (5.89) |
| $G_{max}$ (mg/dl) | 155.84 | 157.44 | 161.18 | 163.15 |
| | (8.13) | (7.01) | (6.12) | (5.86) |
| $G_{min}$ (mg/dl) | 68.57 | 68.80 | 71.79 | 71.13 |
| | (8.64) | (8.46) | (6.14) | (6.44) |
| $AUC_{ins} \times 10^2$ (mU) | 747.55 | 860.57 | 684.24 | 803.16 |
| | (90.36) | (95.13) | (72.84) | (70.74) |
| NSSD (%) | 2.42 | 2.64 | 2.86 | 2.79 |
| | (0.54) | (0.51) | (0.80) | (0.63) |
| $Subjects_{60-50, BG}$ | 13 | 14 | 0 | 0 |
| $Subjects_{BG<50}$ | 0 | 0 | 0 | 0 |
| $Subjects_{160-180, BG}$ | 20 | 25 | 64 | 58 |
| $Subjects_{BG>180}$ | 0 | 0 | 0 | 0 |

In summary, a controller according to one embodiment of this invention has been shown to keep blood glucose concentrations within the desired normoglycemic limits avoiding hyperglycemia and hypoglycemia, even for the most challenging subcutaneous-glucose subcutaneous-insulin route, and for a population with poorly controlled diabetes represented by an insulin resistant group. The algorithm has been tested with GPC and LQC methods to provide effective blood glucose regulation in response to multiple meal challenges with simultaneous challenge on subject's insulin sensitivity.

The invention thus provides a subject-specific adaptive modeling strategy that does not require any physiological representation of glucose-insulin dynamics or disturbance modeling. Glycemic disturbances encountered during daily life and a subject's glucose metabolism can unpredictably vary over wide ranges. The modeling and control algorithms of this invention can dynamically monitor and reject such variable dynamic behavior and different types of glycemic inputs without requiring any prior information about the disturbances. The change detection method is specifically designed to improve the predictions in presence of any changes in blood glucose caused by any type of input or metabolic behavior. Another benefit is that the two time-delays associated with glucose control are explicitly expressed in the formulations of the controller structure. Application of the algorithm to any insulin delivery and glucose measurement route is straightforward since it will require only the adjustment of time-delay values.

Benefits of this invention include that the invention can be subject-specific and does not require any detailed representation of glucose-insulin dynamics, additional disturbance modeling, manual inputs by the patient, or prior experimental data for subject-specific tuning. This approach can improve management with diabetes while reducing the burden of frequent blood glucose testing and insulin adjustments; therefore reducing the development of complications and improving quality of life for patients with type 1 diabetes.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A method of predicting glucose levels in a patient, the method comprising:
   automatically measuring a glucose level in the patient to obtain an actual glucose measurement;
   automatically monitoring a physiological variable of the patient to obtain a measured physiological variable;
   automatically modeling a glucose concentration of the patient as a function of the actual glucose measurement and the measured physiological variable;
   automatically estimating a future glucose level for the patient from the model of the glucose concentration of the patient; and
   automatically updating the model of the glucose concentration as a function of further glucose measurements and further physiological variables.

2. The method according to claim 1, further comprising automatically recursively updating the model of the glucose concentration with each of the further glucose measurements.

3. The method of claim 1, wherein the updating occurs upon determining a difference between the estimated future glucose level for a timeframe and a further actual glucose level at the timeframe.

4. The method of claim 1, wherein the updating of the model comprises modifying model parameters upon comparing the estimated future glucose for a timeframe to the further physiological variables measured during the timeframe.

5. The method according to claim 1, further comprising periodically measuring a glucose level in the patient with a continuous glucose monitor worn by the patient.

6. The method according to claim 1, further comprising monitoring for physiological variables of the patient using at least one sensor worn by the patient that measures movement, skin temperature, dissipated heat from the body, galvanic skin response, or combinations thereof, and further comprising deriving at least one physiological variable selected from sleep, total energy expenditure, stress, physical activity, or combinations thereof.

7. The method according to claim 1, further comprising activating an alarm when an estimated future glucose level is below a predetermined glucose level.

8. The method according to claim 1, further comprising:
   determining changes in glucose concentration model parameters; and modifying the glucose concentration model in view of the new parameters.

9. The method according to claim 1, wherein the method is a closed-loop insulin therapy without manual inputs by the patient.

10. The method according to claim 1, further comprising determining a difference between an estimated future glucose level for a timeframe and an actual glucose measurement for the timeframe, and modifying the model of the glucose concentration as a function of the difference.

11. The method according to claim 1, further comprising measuring the glucose level with a subcutaneous continuous glucose monitor and compensating for time delays between blood glucose levels and subcutaneous glucose levels.

12. The method according to claim 1, further comprising storing the actual glucose measurements and corresponding physiological data on a recordable medium in combination with a data processor, each worn by the patient, and automatically modeling the glucose concentration of the patient with the data processor as a function of a plurality of the stored actual glucose measurements and the corresponding physiological data sampled during a predetermined timeframe prior to the modeling or estimating.

13. The method according to claim 1, further comprising automatically infusing insulin into the patient by modifying an insulin flow rate by an insulin pump.

14. The method according to claim 13, further comprising compensating for time delays between subcutaneous insulin injection and insulin levels in blood.

15. The method according to claim 1, further comprising:
providing a device including an automatic controller in wired or wireless communication with each of a glucose sensor, a physiological sensor, and an insulin pump, each worn by the patient;
the automatic controller automatically collecting information from the glucose sensor to obtain actual glucose measurements;
the automatic controller automatically collecting information from the physiological sensor to obtain measured physiological variables;
the automatic controller automatically recursively modeling the glucose concentration of the patient as a function of the actual glucose measurements and the measured physiological variables;
the automatic controller estimating future glucose levels for the patient from the recursive model of the glucose concentration of the patient;
the automatic controller automatically activating the insulin pump to inject an amount of insulin determined in response to the estimated future glucose level;
obtaining new sensor measurements after injecting the amount of insulin; and
the automatic controller updating the recursive model of the glucose concentration as a function of new sensor measurements and the amount of insulin.

16. The method according to claim 15, wherein the glucose sensor comprises a continuous glucose monitor and the prediction module comprises an algorithm for predicting future glucose concentration values at or between 5 to 30 minutes into the future.

17. The method according to claim 15, wherein the physiological sensor comprises an armband monitoring system worn by the patient.

18. The method according to claim 15, wherein the physiological sensor measures at least one of movement, skin temperature, dissipated heat from the body, galvanic skin response, or combinations thereof, and derives at least one variable selected from sleep, total energy expenditure, stress, physical activity, or combinations thereof.

19. The method according to claim 15, the device further comprising a recordable medium for storing data measured by the glucose sensor and the physiological sensor, and a prediction module that predicts the future blood glucose level using at least a portion of the stored measured information by the glucose sensor and the physiological sensor.

20. The method according to claim 15, wherein the controller comprises a closed-loop system without manual inputs by the patient.

21. The method according to claim 15, the device further comprising an alarm mechanism for alerting the patient of an unsafe current or future glucose level.

* * * * *